United States Patent
Nicoli

(10) Patent No.: US 6,211,956 B1
(45) Date of Patent: Apr. 3, 2001

(54) AUTOMATIC DILUTION SYSTEM FOR HIGH-RESOLUTION PARTICLE SIZE ANALYSIS

(75) Inventor: David F. Nicoli, Goleta, CA (US)

(73) Assignee: Particle Sizing Systems, Inc., Santa Barbara, CA (US)

( * ) Notice: Subject to any disclaimer, the term of this patent is extended or adjusted under 35 U.S.C. 154(b) by 0 days.

(21) Appl. No.: 09/172,675

(22) Filed: Oct. 15, 1998

(51) Int. Cl.$^7$ .................................................. G01N 21/00
(52) U.S. Cl. ........................ 356/337; 356/338; 73/863.01
(58) Field of Search ..................................... 356/337, 338, 356/335, 336, 342; 73/864.12, 863.01; 250/576

(56) References Cited

U.S. PATENT DOCUMENTS

| | | |
|---|---|---|
| 3,567,390 | 3/1971 | Rothermel . |
| 3,979,669 | 9/1976 | Godin . |
| 4,148,859 * | 4/1979 | Simpson et al. ................... 73/422 R |
| 4,794,806 * | 1/1989 | Nicoli et al. ...................... 73/863.01 |
| 5,351,118 | 9/1994 | Spinell . |
| 5,407,269 | 4/1995 | Sherry . |
| 6,007,235 * | 12/1999 | Freud et al. ......................... 366/136 |

FOREIGN PATENT DOCUMENTS

| 0510788A2 | 10/1992 | (EP) . |
|---|---|---|
| 1125317 | 8/1968 | (GB) . |

* cited by examiner

Primary Examiner—Frank G. Font
Assistant Examiner—Roy M. Punnoose
(74) Attorney, Agent, or Firm—Milton M. Field

(57) ABSTRACT

An automatic dilution system and method provides optimal dilution factor DF for a sample suspension containing particles mixed with a diluent. A diluent flows into a mixing chamber, and the sample is injected into the chamber. A sensor, such as a single particle optical sensor (SPOS), measures the value of a particular characteristic, which characteristic $R_{max}(0)$ is the initial rate of increase of a quantity related to particle concentration. A CPU/Controller calculates from $R_{max}(0)$ the optimal value of DF, and develops a control signal which adjusts the flow of the sample to provide the optimal value of DF. In a first embodiment, all of the diluted sample passes through the sensor. In a second embodiment, only a portion of the sample is directed through the sensor to shorten the time to reach equilibrium. The time to reach equilibrium is further reduced in a third embodiment in which the mixing means is a static mixer, having relatively small volume, inserted in series with a diluent flow tube. The sample is injected into the flow tube upstream of the mixer. Larger dilution factors are obtainable in a fourth embodiment in which the sample is first prediluted in a mixing chamber and then further diluted in a second mixing chamber. A fifth embodiment also predilutes the sample, but to shorten the time to reach equilibrium, uses a static mixer for the second dilution stage. In all embodiments, the diluted fluid may be fed to one of two branches, one having an SPOS and the other having a sensor using the light scattering principle.

53 Claims, 11 Drawing Sheets

AUTOMATIC DILUTION SYSTEM FOR HIGH-RESOLUTION PARTICLE SIZE ANALYSIS

BACKGROUND OF THE INVENTION

1. Field of the Invention

The present invention relates to a method and apparatus for automatic dilution of a starting concentrated fluid suspension of particles for the purpose of optimizing a measurement of the particle size distribution, where the measurement technique chosen is sensitive to individual particles in the suspension over some appropriate range of particle size.

2. Description of the Prior Art

There are many intermediate process materials and final products of technical and/or commercial significance which exist either as a relatively high concentration of solid particles or liquid droplets suspended in a fluid, or as powders, which can be suspended in an appropriate liquid. The physical and/or chemical characteristics of these particle suspensions or dispersions (referred to herein as "sample suspensions"), or of the final products derived from them, often depend critically on the particle size distribution (PSD). Hence, it has become increasingly important to determine the PSD of these particle suspensions with high accuracy, resolution and reproducibility, often in the early stages of production. The solid particles or liquid droplets (in the case of oil-in-water or water-in-oil emulsions)—known as the "dispersed phase"—are suspended in an appropriate fluid, consisting of a simple liquid (e.g. water or an organic solvent) or mixture of liquids, perhaps containing one or more additives of various kinds (e.g. surfactants)—known as the "continuous phase". Typically, the starting particle suspensions to be analyzed contain a relatively high concentration of the dispersed phase—usually exceeding 10% by weight or volume of the overall fluid suspension, and sometimes reaching 40–50%.

Most methods of particle size analysis (PSA) require that the sample presented to the analyzer be much less concentrated than that which is typically available from an intermediate process stream or final product. This requirement that the starting sample be diluted, sometimes very substantially, prior to determination of its PSD is particularly critical for methods known as single-particle sensing (SPS) techniques. Because these methods demand relatively low concentrations of suspended particles in order to produce PSD results of high accuracy and minimal distortion, they are effective in providing a motivation for the present invention.

The well-known method of single-particle optical sensing (SPOS), described extensively elsewhere, is one particular kind of SPS method. It utilizes the principle of either light extinction or scattering to determine the mean diameters of suspended particles as they pass individually through a very small sensing "zone" or "view volume". In the recent invention of Wells et al (pending U.S. patent application Ser. No. 08/625,540, filed May 28, 1996, now U.S. Pat. No. 5,835,211), the physical principle of light scattering is combined with that of light extinction in order to increase the sensitivity and dynamic size range of the sensor. The resulting hybrid design thus extends the applicability of the SPOS method to particles smaller than those which would be detectable using only the light extinction technique, while preserving the large size range offered by the latter. This improvement increases the usefulness and overall effectiveness of the SPOS method.

There is another well-known SPS method for particle size analysis which is based on a different physical principle—the "electro-zone", or "Coulter counter", method. In this well-known technique, one monitors the conductivity between two volumes of partially conducting liquid, one of which contains the suspended sample particles at relatively low concentration, connected together by a small pore. The conductivity decreases momentarily whenever a particle passes through the connecting pore, caused by a pressure differential applied between the two liquid volumes. The magnitude of the conductivity decrease is proportional to the volume of the particle which momentarily interrupts the current flow through the pore. This represents another viable SPS method which can be used in conjunction with an autodilution system based on the present invention.

Regardless of the specific SPS method which is used to perform a PSA measurement, a concentrated particle suspension typically requires extensive predilution in order to ensure accurate PSD results with minimum distortion and artifacts. Specifically, this step is needed to ensure that the particles pass through the active sensing volume, or zone, one at a time, thereby avoiding all but occasional "coincidences" and consequent distortions of the output signal pulses and resulting PSD. For the purpose of explaining the underlying principles of this invention, it is convenient to focus exclusively on the use of an SPOS-type sensor in conjunction with the automatic dilution method and apparatus to be described. However, no loss of generality is thereby intended or implied. Rather, it is implicitly assumed that other methods of particle size analysis, including but not limited to other SPS methods, such as the electro-zone technique, may be used in place of the SPOS method in conjunction with this invention. Examples include "ensemble-type" methods for PSA, which respond to many particles at the same time, such as dynamic light scattering (DLS) and Fraunhofer diffraction (FD), also known as "laser" diffraction (LD). These techniques also usually require substantial dilution of concentrated particle suspensions, depending on their composition and particle size range (i.e. PSD). However, the extent of dilution typically required for these ensemble techniques is often considerably smaller than that needed for SPS techniques, such as SPOS and electro-zone sensing.

Therefore, PSA measurements, including those performed using the SPOS method, generally require substantial dilution of the original concentrated particle suspension, using an appropriate fluid, or mixture of fluids, as a diluent. This is especially required for automatic "online" particle size analysis of process suspensions in a production environment. In this case a dilution system should be able to accommodate samples with greatly differing PSDs, without requiring knowledge of their concentration, composition or PSD characteristics. The extent of dilution of the starting sample should be arrived at quickly and be optimal for the particle size analysis method being utilized—e.g. SPOS.

There are numerous applications for PSA in which the concentration of the starting particle suspension changes relatively little from one sample to the next. In such cases, it may be sufficient to dilute the starting particle suspension using a fixed, predetermined dilution factor, DF. This fixed DF value can be determined ahead of time, in trial-and-error fashion, for each kind of sample or application. A variety of prior art methods and devices exist for diluting a fluid sample with a predetermined dilution factor. By definition, these prior art methods and devices cannot provide for variable dilution when such would be more useful than the fixed, predetermined dilution which they provide, and therefore they are of limited utility.

Examples of prior art methods and/or devices which can be used to provide a fixed, predetermined dilution of fluid samples are described in: Cruzan, U.S. Pat. No. 4,036,062, Roof et al, U.S. Pat. No. 4,036,063, and Roof, U.S. Pat. No. 4,070,913. All of these patents describe means for diluting a fluid sample with a diluent fluid in which each of the fluids is initially contained in separate conduits. At the start of the dilution process the two conduits are connected together to permit closed-loop circulation and mixing of the two fluids. The extent of dilution— i.e. the value of the dilution factor, DF—is determined ahead of time by preselecting the volumetric relationship (relative volumes) of the two conduits.

This traditional approach to diluting a starting concentrated particle suspension is, by definition, inflexible and therefore quite limited. It is also potentially inaccurate when relatively large dilution factors are required. In such situations it may be problematic to inject, or meter out accurately, a very small volume of starting particle suspension into a much larger volume of diluent fluid. This limitation can in general be overcome by performing multiple dilutions in succession, where each dilution step has a fixed, relatively small DF value, able in principle to be accurately controlled. The final dilution factor is then equal to the product of all of the individual, intermediate DF values. However, the apparatus needed to implement this multiple-dilution approach is necessarily more complex and difficult to maintain than a simple, single-stage dilution device.

There exist prior art dilution systems which introduce both the starting concentrated fluid sample and diluent fluid into a mixing chamber on a continuous basis. The rates of flow of each of these input components can be adjusted to fixed, known values so as to yield a final diluted fluid sample having a known dilution factor DF equal to the ratio of the total fluid flow rate (diluent plus starting concentrated sample) to that of the starting concentrated sample alone. The final diluted sample suspension is typically extracted from the mixing chamber at a steady flow rate. Such a dilution system, having a known, but adjustable, dilution factor, is described in the invention of Mowery, Jr., U.S. Pat. No. 4,095,472. In this patent a fixed dilution factor is established at the start of the dilution process. In principle, the dilution factor can range from a relatively low value to a very high one. This method will be described in greater detail subsequently. The invention of Culbertson, U.S. Pat. No. 3,805,831, describes an apparatus for continuously and proportionately mixing one fluid stream, containing concentrated solute, with another, acting as the diluent. The final solute concentration which emerges in the resulting fluid stream is determined by the composition of each individual fluid stream and their relative rates of flow.

Automatic dilution systems which rely on the principle of negative feedback have also been described. In these systems, one or both of the flow rates of the starting, concentrated solute sample and the diluent fluid which enter the mixing chamber are continuously adjusted so as to yield an approximately unchanging solute concentration in the fluid mixture which exits the chamber. Mechanisms for adjusting the flow rate(s) have been proposed which respond to a measurement of the turbidity (i.e. optical density, or absorbence, at a particular wavelength or range of wavelengths) or scattered light intensity (over a particular range of angles) or diffracted light intensity obtained from the diluted fluid mixture residing in, or exiting from, the mixing chamber. A dilution system which responds to one of these measurements is implied by the invention of Pardikes, U.S. Pat. No. 4,279,759, which describes the use of optical sensing devices to measure the presence of a treatment chemical in a liquid process stream. Using negative feedback, this invention controls the rate of introduction of the treatment chemical into the continuously flowing stream so as to establish a relatively fixed, but adjustable, concentration of the chemical in the stream. By extension, sensing techniques based on light scattering and/or diffraction, as described in the inventions of Moreaud et al, U.S. Pat. No. 4,348,112, Tsuji et al, U.S. Pat. No. 4,408,880, and Brenholdt, U.S. Pat. No. 4,507,556, can be used to adjust the flow rate(s) of one or both of the starting concentrated fluid sample and diluent fluid entering a mixing chamber for the purpose of holding relatively constant the solute concentration in the resulting diluted sample fluid.

Finally, the method and apparatus described in the invention of Nicoli et al, U.S. Pat. No. 4,794,806, is able to dilute a starting concentrated particle suspension, using the principle of (approximate) exponential dilution of particles suspended in fluid in a mixing chamber of fixed volume due to the continuous addition of a diluent fluid at a known flow rate. Unlike the methods and devices described above, based on continuous mixing of both the concentrated sample fluid and the diluent fluid, the method described by Nicoli et al is based on injection of a fixed amount of sample into the mixing chamber. Hence, the amount of diluted sample material (i.e. suspended particles) available for the PSA measurement process at the output of the mixing chamber is limited by the amount which was originally injected into the chamber at the start of the automatic dilution process.

SUMMARY OF THE INVENTION

This invention is directed toward a new and novel method and apparatus for optimizing the extent of dilution to be applied to a starting concentrated particle suspension, for the purpose of carrying out a relatively fast and efficient particle size analysis (PSA) of same, preferably using a single-particle sensing (SPS) technique—for example, that of single-particle optical sensing (SPOS). In particular, this new method permits fast, virtually real-time optimization of the dilution factor DF for each sample to be analyzed, thereby shortening the total time needed for dilution and subsequent analysis of the sample. An automatic dilution system based on this invention is able to optimize the dilution factor shortly after the start of injection of a concentrated sample suspension into a mixing chamber in order to arrive at an optimal, steady-state (equilibrium) particle concentration in the mixing chamber or in the fluid stream exiting therefrom, which can be analyzed immediately thereafter using an appropriate SPS-type sensor.

As indicated above, for the purpose of describing this invention it is convenient to focus on the SPOS method of particle size analysis, based on the physical principle of light extinction or light scattering or some combination thereof (as described in the Wells et al U.S. Patent application). The particle concentration in the fluid stream passing through the SPOS sensor can be expressed either as the total number of particles, or the number in a given size range, per unit volume of fluid suspension. In general it must be large enough on the one hand to dominate over spurious particle counts due to background contaminants in the diluent fluid or statistical fluctuations due to insufficient particles in a given size range, but small enough, on the other hand, to avoid significant particle coincidences—i.e. two or more particles entering the "view volume" of the SPOS sensor at approximately the same time, thereby potentially causing distortions in the resulting PSD.

It is useful to review in detail the prior art method of diluting a concentrated "sample fluid" (particle suspension)

by continuously combining it in a mixing chamber with an appropriate diluent fluid. This steady-state, "mixed-flow" approach is the starting point for the present invention. The fluid contents of the mixing chamber are continuously and efficiently mixed, so that ideally the particle concentration, expressed either as the total number of particles, or the number in any given size range, per unit volume of fluid suspension, is always homogeneous throughout the mixing chamber. The "sample fluid" continuously injected into the mixing chamber is the starting concentrated suspension of particles of a given composition and particle size distribution (PSD), where the suspending fluid is typically water or some organic liquid or mixture of liquids. The second fluid continuously injected into the mixing chamber consists of relatively particle-free diluent, with which one wishes to dilute the starting sample suspension. All or part of the fluid/particle mixture exiting the mixing chamber is made to flow, at an appropriate rate, through a suitable sensor, designed to respond to individual particles in the diluted output stream, producing a signal which can be processed to obtain the PSD. A simplified diagram of the dilution scheme is shown in FIG. 1. In general one must reduce the particle concentration of the starting suspension in order to minimize the likelihood of coincidences and thereby optimize the quality of the PSA results.

Owing to conservation of fluid, the rate of flow F of the diluted particle suspension exiting the mixing chamber MC equals the sum of the two individual rates of flow, $F_D$ and $F_S$, of diluent and concentrated particle suspension which enter the chamber through tube 12 and tube 10, respectively. Thus, $$F=F_D+F_S \tag{1}$$

The particle suspension residing in, or exiting through port 11 from, the mixing chamber MC is less concentrated than the original particle suspension which enters mixing chamber MC through tube 10, where the extent of dilution is described by the dilution factor DF, which equals the ratio of the (volumetric) rate of flow of the output fluid F through tube 11 to the (volumetric) rate of flow of the starting concentrated particle suspension $F_S$, provided that steady-state equilibrium conditions have been reached in the mixing chamber MC, resulting in an approximately constant particle concentration, $$DF=F/F_S=1+F_D/F_S \tag{2}$$

For many important applications involving relatively highly concentrated sample suspensions, the desired dilution factor DF will be relatively high—i.e. DF>>1—so that $F_D>>F_S$. In such cases the flow rate F of diluted particle suspension exiting the mixing chamber MC will be approximately equal to the flow rate of diluent fluid entering the mixing chamber—i.e. $F \approx F_D$. In this case, $DF \approx F_D/F_S$.

Equation 2 above is valid provided that sufficient time has elapsed that the particle concentration in the mixing chamber has reached steady-state equilibrium. Immediately following the start of flow of the sample suspension into the mixing chamber (defined as t=0), assuming that it already contains a volume V of clean, particle-free diluent and that fresh diluent is also flowing into the mixing chamber at a steady flow rate $F_D$, the particle concentration in the fluid stream which exits the mixing chamber, defined here as C(t), increases monotonically with time t. Assuming ideal mixing of the fluids in the mixing chamber, the output particle concentration C(t) is described by, $$C(t)=(C_0/DF)[1-e^{(-t/\tau)}] \tag{3}$$

where $C_0$ is the particle concentration of the starting sample suspension being injected into the mixing chamber, expressed either as the total number of particles, or the number in a given size range, per unit volume of fluid suspension. Parameter $\tau$ is the characteristic time constant, commonly referred to as the "decay time", or "residence time", of the chamber. Quantity $\tau$ characterizes the rate at which the particle concentration in the mixing chamber (and hence in the output fluid stream) approaches its final equilibrium value $C_0/DF$ and is given by, $$\tau=V/F \tag{4}$$

Here, V is the total volume of fluid (including particles) in the mixing chamber which participates in the mixing process and F is the combined rate of flow of sample suspension and diluent fluid entering the mixing chamber under steady-state conditions, given by Equation 1. The behavior of C(t) with increasing time t following the start of injection of the sample (assuming that diluent fluid is flowing) is shown in FIG. 2. In most cases of practical interest a relatively large dilution factor, DF>>1, is required. In such cases $F_D$ is much larger than $F_S$, and hence $\tau$ is approximately equal to $V/F_D$.

As indicated by Equation 3, a period of time must elapse following initial injection of the concentrated sample suspension in order for the particle concentration in the mixing chamber, and therefore in the output fluid stream exiting the mixing chamber, to reach a nearly constant, equilibrium value, given by $C_0/DF$. This time must exceed considerably the characteristic "residence" time $\tau$ of the mixing chamber, which is a measure of the average time that a newly-injected particle resides within the mixing chamber before exiting in the output fluid stream. For example, after a total elapsed time of $3\tau$, assuming ideal fluid mixing, the particle concentration in the output fluid stream is given by $(C_0/DF)(1-e^{-3})=0.95\ C_0/DF$—i.e. 95% of the theoretical steady-state value. Alternatively, after an elapsed time of $5\tau$, the particle concentration in the output fluid equals 0.993 $C_0/DF$, which is less than 1% away from the final value.

The detailed "shape" of the PSD of the diluted particle suspension which exits the mixing chamber, $f_{OUT}(d)$ vs d, should precisely mimic the shape of the PSD of the starting sample suspension injected into the chamber, $f_{IN}(d)$ vs d, where d is the mean particle diameter, assuming an ideal, random mixing process. In particular, one expects, $$f_{OUT}(d)=(1/DF)f_{IN}(d) \tag{5}$$

where both $f_{IN}(d)$ and $f_{OUT}(d)$ describe the number of particles of diameter d—i.e. in a very small range of diameters, $\Delta d$, centered at d—per unit volume of fluid/particle suspension. That is, the PSD of the diluted particle suspension should ideally be identical to the PSD of the starting sample, except that the absolute number of particles measured per unit volume of liquid in each "channel", or interval, of particle diameter $\Delta d$ for the diluted sample is simply reduced by a factor of 1/DF with respect to the absolute number of particles per unit volume of the original sample suspension.

There are two attributes of this mixed-flow dilution method which are noteworthy. First, by its nature, it is a "steady-state" method, able to produce diluted sample suspension on a continuous basis, as long as one is able to deliver concentrated sample suspension and fresh diluent to the mixing chamber at their respective steady flow rates. The dilution factor is presumed to be adjusted so as to yield a particle concentration appropriate for the PSA measurement (e.g. SPOS), given the features of the PSD which one wishes to obtain. (The definition of an "optimal", appropriate concentration will be discussed below.) One is free to dilute and measure as much starting sample suspension—i.e. as many sample particles in a given particle size range—as desired, depending on the time available and the kind and quality of the PSD results desired. All that is required is to operate the dilution system continuously, on a steady-state basis, with continuous injection into the mixing chamber of the concentrated sample suspension at some chosen flow rate $F_S$, and continuous injection of filtered diluent fluid at another chosen flow rate $F_D$.

There is a second key attribute of the mixed-flow method of sample dilution. Namely, it makes possible a new type of automatic dilution system which, for example, is very effective for analyzing certain key features of a broad class of particle size distributions. The present invention proposes the use of a specific and unique control mechanism to provide fast and automatic adjustment of the dilution factor DF, so as to optimize, quickly and efficiently, the particle size analysis measurement. This turns out to be especially important, for example, when one wishes to explore certain portions of the PSD of "mostly-submicron" emulsions and dispersions, for which the SPOS-PSA system is used to detect and analyze only a relatively small fraction of the overall particle population (i.e. only the largest diameters), as will be discussed subsequently.

It is often advantageous, if not essential, to reduce the overall time for dilution and subsequent measurement of a particle suspension, consistent with one's ability to obtain accurate PSD information with acceptable statistical accuracy, based on the total number of particles counted in each interval, or "channel", of particle diameter, $\Delta d$. Reduction of the overall time needed to dilute and analyze a sample is clearly advantageous for laboratory applications involving large batches of samples. However, it becomes critically important for applications involving online process monitoring. The continuous mixed-flow dilution method, which forms the starting point for the present invention, permits the PSA instrument to make a dynamic decision, right after the start of the dilution process, in order to calculate and apply an optimal dilution factor DF and also, if desired, to estimate how much sample to analyze, by examining certain features of the PSD, which can be constructed in real time during the early acquisition of particle count/size data. This capability contrasts with other methods of sample dilution, such as the one described in Nicoli et al, U.S. Pat. No. 4,794,806, in which the total amount of sample material available for measurement and analysis is typically limited, equal to that which has initially been introduced into the mixing chamber of the dilution system.

Adjustment of the dilution factor DF is typically accomplished by varying the flow rate $F_S$ of injection of concentrated sample suspension into the mixing chamber, with the flow rate $F_D$ of injection of fresh diluent into the latter held constant. (Alternatively, and usually less desirably, the value of DF can be adjusted by varying the flow rate $F_D$ while holding flow rate $F_S$ constant; or both flow rates can be adjusted in such ways that the ratio $F_D/F_S$ achieves the desired value.) The point of being able to adjust the quantity DF in the first place is to be able to set it to an "optimal" value, or within a range of such values—i.e. so that the resulting particle concentration is "optimal" for the PSA measurement.

The diluted particle concentration is said to be "optimal" for an SPOS-type measurement in a very specific sense. It is generally chosen to be the concentration at which the SPOS sensor is able to perform most effectively—i.e. yielding a signal which produces PSD results of maximum accuracy and resolution, requiring minimum analysis time. In the case of an SPOS-type PSA measurement, the most important factor to consider is the "coincidence" limit, or concentration, of the sensor. This quantity is based principally on the optical and signal-processing design of the sensor and secondarily on the characteristics of the underlying PSD of the sample.

An example may be useful. In a representative, commercially available light-extinction sensor (Model LE400-1.3, Particle Sizing Systems, Santa Barbara, Calif.), the cross-sectional dimensions of the flow-through cell are (approx.) 400 $\mu$m×1000 $\mu$m. A thin "sheet" of laser light, of thickness approximately 35 $\mu$m (defined by the $1/e^2$ intensity points), cuts across the flow channel in perpendicular fashion. The resulting thin "slab" of illumination, which defines the active sensing zone, or "view volume", of the sensor has a volume $\Delta V$ equal to 400 $\mu$m×1000 $\mu$m×35 $\mu$m, or $1.4\times10^{-5}$ cm$^3$. The dilute liquid-particle suspension passes through the flow channel, typically at a flow rate of 1–2 ml/sec, causing the particles to pass momentarily through the view volume. The passage of each particle gives rise to an output signal pulse, the magnitude of which depends on the size (and, to a lesser extent, the composition) of the particle as well as the detection principle employed (i.e. light extinction, light scattering, or some combination thereof) and the details of the sensor design.

For most PSA applications using the SPOS method, one wishes to avoid particle "coincidences"—i.e. the passage of two or more particles through the active sensing zone of the sensor at the same time. This preference, of course, is designed to reduce the likelihood of distortion of the pulse height distribution and corresponding computed PSD. In the case of the example above, if the particles were "ideally" distributed throughout the suspending liquid, they would arrive at the active sensing zone spaced equally apart in distance (and in time of arrival). They would then pass individually through the sensing zone provided the concentration didn't exceed $1/\Delta V$, or approximately 70,000/ml. Using this ideal (unrealistic) assumption, each view volume could be said to be "occupied" by a single particle.

In practice, of course, the particles are located randomly throughout the suspending liquid, thus greatly increasing the likelihood of coincidences occurring within the sensing zone and of consequent distortions in the heights of a fraction of the signal pulses. Hence, in order to reduce the probability of particle coincidences, it is necessary to reduce significantly the working concentration of the sample suspension. As a rule of thumb, a reduction to 1/10 of the concentration computed above ($1/\Delta V$) is usually deemed sufficient to alleviate this problem. This reduces the approximate frequency of coincidence events to less than 1% of the total number of signal pulses. Using the example above, this translates to a suggested concentration limit of approximately 7,000 particles/ml. This estimate is relevant for small particles, having dimensions significantly smaller than the width of the active sensing zone (assumed to be 35 $\mu$m in the example above). In the case of particles larger than the zone thickness, the concentration at which the frequency of coincidences lies below the 1% level decreases with increasing particle size.

Finally, it should be appreciated that in theory there is no lower limit on the final particle concentration which can be adopted by the dilution systems herein described for use in an SPOS-type measurement. At arbitrarily low particle concentrations there is a vanishingly low probability of the occurrence of particle coincidences and therefore of distortions in the resulting PSD. However, in practice there are two obvious, major disadvantages associated with such a "conservative" approach of choosing a very large dilution factor DF (i.e. much lower than the nominal coincidence limit of the sensor would dictate). First, it would be necessary to filter the diluent extensively, in order to ensure a very low concentration of contaminant particles occurring naturally in the diluent. Otherwise, the resulting PSD will not be representative of the starting sample, but instead may be distorted significantly by the presence of spurious particles in the diluent, rather than the sample.

Second, in any case it would be necessary to increase the duration of the measurement, perhaps greatly, in order to achieve adequate accuracy/reproducibility of the resulting PSD. Otherwise, statistical fluctuations in the particle count values in some of the diameter "channels" may prove to be unacceptably large from one measurement to the next, owing simply to the no inadequate number of particles available for counting in any given range of particle diameter.

For most applications of practical interest it is wise, if not necessary, to "optimize" the dilution factor DF so that the final particle concentration in the diluted sample suspension is below the coincidence limit of the sensor, as described above, but not so low as to invite unacceptable levels of noise/distortion in the resulting PSD, resulting either from diluent impurities or statistical fluctuations due to insufficient sample particles. Typically, these considerations translate into choosing a final particle concentration in the range of 20% to 80% of the nominal coincidence limit of the sensor. Using the example above, this would be equivalent to a concentration of 1400 to 5600 particles/ml. However, in specific applications which require enhancement of the sensitivity of the PSA measurement to the small fraction of largest particles in the PSD, comprising the "tail" of the latter, it is often advisable or necessary to increase the working particle concentration to a value well above the levels indicated above. This point will be discussed more fully later.

Optimization of the dilution factor DF for an SPOS measurement is accomplished using a specific control "signal", in order to control the flow rate $F_S$ of injection of the sample suspension (or, alternatively, the flow rate $F_D$ of the diluent). The optimal value of DF is based on specific requirements of the SPOS sensor (i.e. its coincidence limit) as well as possibly particular characteristics of the PSD of the sample being diluted and analyzed (discussed below). The control signal which is used to determine an acceptable/optimal value for the dilution factor DF is derived from the count rate of particles detected by the SPOS sensor as well as possibly specific details of the PSD which is generated from the pulse count/height information. This specific use of the particle count rate—or, equivalently, the corresponding particle concentration—over a specific range of particle sizes to determine the dilution factor at the start of a PSA measurement constitutes the new and novel method which forms the basis of this invention. The effective "feedback" control signal is obtained by suitably processing the pulse output signal provided by the SPOS sensor which is able to sample all or part of the output flow stream exiting the mixing chamber or its internal fluid/particle contents. This approach provides a valuable attribute: the ability to adjust the dilution factor automatically and quickly, on an approximately real-time basis, for each new sample introduced into the automatic dilution system.

The equilibrium particle concentration which is effectively reached in the mixing chamber, or in its fluid output, after several $\tau$ residence times r have elapsed can be estimated reasonably well in a relatively short time, following commencement of dilution of the starting sample, as will be described below. This means that an early, "mid-course" correction in the value of the dilution factor DF can be made after a relatively short time has elapsed, thus enabling the value of DF to be readjusted, possibly to a much smaller or larger value, in order to save time and "zero in" on a final, optimal value for DF much faster than would otherwise be the case. An alternative, "brute-force" approach consists of "guessing" a trial value for DF, waiting for approximate equilibrium in the output particle concentration to be reached, readjusting the value of DF, waiting a similar length of time for equilibrium to be reestablished, and then possibly repeating this sequence in order to arrive at an appropriate extent of dilution of the sample suspension. The disadvantage associated with this simple iterative procedure of trial-and-error selection of the dilution factor DF—apart from its obvious time-consuming nature—is that the output signal response from a typical SPOS-type sensor becomes highly nonlinear with particle concentration once the latter substantially exceeds the coincidence limit. The measured pulse rate can actually decrease with increasing particle concentration in certain ranges of concentration due to the effects of more frequent particle coincidences (resulting in more frequent merging of adjacent signal pulses). Therefore, a simple trial-and-error approach of setting the dilution factor DF, by observing the effect of increasing or decreasing sample dilution on the pulse output of an SPOS sensor, may turn out to be convoluted, as well as time-consuming.

From the discussion above it is evident that an estimate of the final, steady-state (equilibrium) value of the diluted particle concentration can be made quickly, immediately after the onset of the dilution process. Following initial injection (t=0) of the concentrated sample suspension into the mixing chamber, particles will begin to appear in the output fluid stream with increasing concentration, C(t), as described ideally by Equation 3. The instantaneous rate of increase R(t) of the particle concentration with time is given by the time derivative of C(t)—dC(t)/dt. From Equation 3 one calculates, $$R(t)=dC(t)/dt=(C_0/DF)(1/\tau)e^{(-t/\tau)} \tag{6}$$

where $\tau=V/F \approx V/F_D$ for $F_D >> F_S$, as discussed earlier.

Clearly, the maximum value of the rate of increase in particle concentration occurs at t=0—essentially immediately after the start of injection of the concentrated sample suspension. This maximum rate, defined as $R_{MAX}(0)$, is ideally given by $$R_{Max}(0)=(C_0/DF)/\tau=(C_0/DF)(F/V) \tag{7}$$

This relationship permits easy estimation of the final concentration $C_0/DF$ that should be achieved by the continuous dilution system, assuming that one has waited long enough (i.e. approx. $2\tau$–$3\tau$) to ensure that the particle concentration in the diluted sample suspension residing in, and exiting from, the mixing chamber has reached essential equilibrium and therefore approximate constancy. Solving Equation 7 for the final equilibrium concentration $C_0/DF$, one obtains, $$C_0/DF=\tau R_{MAX}(0)=(V/F)R_{MAX}(0) \tag{8}$$

Because $\tau$ is known—from the constant value of V and the known value of F (approx. equal to $F_D$, for $F_D >> F_S$)—all that remains for fast estimation of $C_0/DF$ is measurement of $R_{MAX}(0)$. In practice this is easily accomplished by counting all particles (either in the total size range accessible by the SPOS-type sensor or in some specified range of sizes, depending on the application in question and desired mode of particle size analysis) over a suitably short time interval $\Delta t$, and corresponding fluid volume, $\Delta V$ (given by $F\Delta t$), where $\Delta t$ is chosen to be large enough to ensure measurement of a statistically-significant number of particles, but significantly smaller than $\tau$—say, $\tau/3$ or $\tau/5$. This measurement is made following initial injection of the starting concentrated sample suspension—in practice, starting at the time when the first significant increase in signal pulses due to particle counts appears in the sensor output. The initial rate, $R_{MAX}(0)$, can then be estimated by computing the ratio $\Delta C/\Delta t$, where $\Delta C$ equals the number of particles counted per unit volume of liquid suspension exiting the mixing chamber and passing through the SPOS sensor.

One can then use this information of estimated final particle concentration $C_0/DF$ to adjust the dilution factor DF, upward or downward, in order to optimize the final particle concentration in the liquid suspension according to the technical specifications and requirements of the sensor and the needs dictated by the specific measurement application and the shape of the PSD (discussed below). In principle, the time which is needed to make this estimation and subsequent adjustment in the dilution factor DF—typically through adjustment of the rate of injection $F_S$ of the starting sample suspension—is significantly shorter than $\tau$, and in any case much shorter than the time needed to reach steady-state equilibrium and essential constancy of the output particle concentration.

This invention, especially when used in conjunction with the SPOS method of particle size analysis, is very useful for determining certain features of the PSD which relate directly to the quality of a wide variety of particle suspensions and dispersions, as discussed further below. These materials have PSDs which vary greatly in "polydispersity" (range of particle size) and complexity (i.e. shape). An important feature of the automatic dilution system of the present invention is that it can establish an optimal extent of dilution of the sample based on information which is obtained from the population-, or number-weighted, PSD during the preliminary stages of the dilution process.

This invention permits optimization of the extent of dilution of a starting concentrated sample suspension based on a measurement of the particle count rate (# particles/sec) obtained from an SPOS-type sensor for a particular flow rate of a diluted suspension or, alternatively, the particle concentration (# particles/ml) for a specific range of particle diameters, where the selected size range may depend on the application or kind of sample in question. This information is used to generate an appropriate "control signal" which is used to influence the dilution system (e.g. the sample injection flow rate $F_S$) by adjusting the dilution factor DF. In this sense, the proposed method effectively employs the principle of "negative feedback". The extent of dilution of the starting sample is influenced by the coincidence concentration limit of the SPOS-type sensor, as discussed above. However, choice of an optimal value for the dilution factor may be influenced by certain features of the underlying PSD of the sample, as determined by a rapid, preliminary measurement of the PSD. The relevant features of the PSD which are used to establish an optimal value for the dilution factor of the system are often inaccessible using other kinds of measurements, sometimes even including other (non-SPS) particle sizing techniques. This is an important advantage of the present invention.

In order to further enhance the understanding of this invention, based on automatic dilution of concentrated samples using one or more techniques for particle size analysis, including the SPOS technique for counting and sizing particles, it is useful to focus on the SPOS method and divide the applications for PSA into two broad categories. The first category consists of samples in which most of the particles (if not all of them) lie within the size range covered by the SPOS sensor. The second category consists of samples in which most of the particles lie below the minimum measurable diameter of the SPOS sensor, designated here as $d_{MIN}$.

In the first case, illustrated schematically (three examples) in FIG. 3, the great majority of particles in the sample are larger than $d_{MIN}$. The entire PSD can therefore be analyzed using the SPOS technique, provided the starting "threshold" diameter for the analysis, shown as $d_o$ in FIG. 3, is chosen to be smaller than the great majority of particles in the sample. Particle count and size data can then be collected for all particle diameters $d \geq d_o$, as previously described.

Three representative number-weighted PSDs which fall into this first broad category of applications are illustrated schematically in FIG. 3. Curve "A" is a simple "unimodal" PSD, similar to that which is often encountered for a wide variety of applications. It is "ideal" in the sense that there is a negligible fraction of particles occupying either the coarse or fine end of the diameter scale. Samples of "good" quality often possess PSDs which resemble "A", requiring only two parameters for characterization—mean diameter and standard deviation (half width), either number- or volume-weighted.

The PSD represented by curve "B" in FIG. 3 differs from "A" in that it contains a greater number of large, "outlier" particles, which define the large-diameter "tail" of the distribution. Particles in this tail region are typically either agglomerates of the smaller "primary" particles or are oversize primaries resulting from insufficient miling or grinding, in the case of powders, or incomplete homogenization, in the case of oil-in-water emulsions, to name only two processes. The quantity of interest is usually the volume fraction of particles associated with the tail of the PSD—i.e. for which $d > d_1$ (FIG. 3), where $d_1$ is chosen to be appropriately larger than the peak or mean diameter of the PSD, where the precise value chosen depends on the detailed shape of the PSD and the nature of the application at hand. This volume fraction often correlates strongly with the quality or stability of a product containing these particles.

Finally, the PSD indicated by curve "C" differs from "A" in that it contains an additional, relatively large fraction of particles of very small diameter, on a number-weighted, or population, basis. These "fines" may have a small, or even negligible, influence on the volume-weighted PSD. Therefore, they frequently escape detection by analysis techniques which are sensitive to particle volume, rather than number. However, their presence often significantly influences the physical and/or chemical properties of final products based on these particles.

For any of the PSDs shown in FIG. 3, choice of an appropriate dilution factor DF for an automatic system based on the mixed-fluid dilution method outlined above is relatively straightforward. If one wishes to use the SPOS technique to "capture" most of the underlying PSD, one must choose a relatively low threshold diameter $d_o$ for the PSA measurement. In this case the sensor will respond to particles of essentially all diameters passing through it. The automatic dilution system would vary the dilution factor DF, typically by adjusting the sample injection flow rate $F_S$, so that the final concentration of particles, over essentially the entire size range, reaches a preset value, equal (approximately) either to the coincidence concentration limit of the SPOS sensor being utilized, or some fraction thereof The extent to which one stipulates ahead of time how much lower the final concentration should be relative to the coincidence limit will depend on how much one wishes to minimize distortions and artifacts in the measured PSD, at the expense of better statistical accuracy. If a conservative PSA measurement is desired, with truly negligible distortion of the PSD due to particle coincidence, one might choose as the "optimal" final particle concentration to be achieved by the automatic dilution system a value substantially below the nominal coincidence limit of the sensor: e.g. 50%, 25%, or even 10% of the latter concentration.

Alternatively, one may wish to perform the PSA measurement in such a way as to improve the statistical accuracy of the tail portion of the PSD, defined by $d \geq d_1$, where, by definition, the number of particles represents a small fraction of the total number of particles in the sample, over the entire size range. One would increase the starting threshold diameter of the SPOS measurement from $d_o$, located below the start of the entire PSD, to $d_1$, located significantly above the peak or mean diameter of the PSD, in order to "amplify" the differences between samples "A" and "B" in FIG. 3. One could then choose a final sample concentration well above the nominal concentration limit of the sensor, in order to increase the absolute number of particles larger than $d_1$ which are available for counting and sizing. However, as a consequence of this higher concentration, one should expect significant distortion in the resulting PSD, with much of the measured distribution shifted to higher diameters. Depending on how steeply the particle number falls off with increasing diameter above $d_1$, the extent of the distortion in the computed PSD for diameter values larger than $d_1$ may or may not be relatively small and therefore tolerable, given the improvement in statistical accuracy, and therefore resolution, of the tail portions of the PSD achieved for samples "A" and "B". The effects of particle coincidences on the distortion of the measured PSD for final particle concentrations larger than the nominal coincidence limit of the SPOS sensor will be discussed in greater detail below, in connection with FIGS. 4A and 4B.

There is a final, important point to be made concerning the choice of an "optimal" dilution factor DF for applications which fall into the first broad category, discussed above. Because the SPOS measurement is sensitive to essentially all of the particles comprising the PSD, determination of an optimal DF value might be accomplished by measuring a property of the diluted sample suspension other than the particle count rate or, equivalently, the particle concentration over the entire measurable size range. Such a property, for example, might be the optical turbidity, or transmittance, of the diluted sample suspension over some range of wavelengths. The measured property might also be the intensity of scattered light produced by the suspension over some range of angles. Alternatively, the monitored quantity might be the volume or mass fraction of the diluted sample suspension, obtained from a densitometer. The relevant point is simply the fact that, for a given type and composition of sample material, the overall particle concentration of the sample can be inferred from a variety of physical parameters other than the number of particles per unit volume of diluted suspension accessible using the SPOS technique.

Hence, while the automatic dilution method which forms the basis for this invention remains useful for analyzing samples with PSDs similar to those shown in FIG. 3 (where most or all of the particles in the sample are larger than the minimum diameter accessible by the SPOS sensor), it is not necessarily indispensable for successful PSA analysis of such samples using the SPOS technique. An appropriate value for the dilution factor DF which ensures successful SPOS analysis of such samples might also be obtained from some physical measurement other than particle counting by the SPOS method, such as those suggested above. The only requirement is that such an alternative measurement also be responsive to the particles over the entire range of sizes comprising the sample, to which the SPOS measurement following automatic dilution of the sample will also respond.

One may therefore better understand the motivation for this invention by considering a second broad category of PSA applications, for which the automatic dilution method, used in conjunction with the SPOS analysis technique, is especially useful—even indispensable in some cases. In this second category the majority of particles to be analyzed using the SPOS technique are assumed to be smaller than the minimum measurable size of the SPOS sensor being utilized.

For the sake of simplifying this discussion, and considering the fact that the lowest practical size limit for SPOS sensors which are useful for the most important applications typically lies somewhere in the range of 0.5–1 $\mu$m (micron), it is convenient to refer to these second-category samples, or applications, as "mostly-submicron". This implies that most of the particles in the sample suspensions of interest are smaller than one micron in mean diameter.

The significance of these "mostly-submicron" PSDs is that for many important applications involving ultra-fine, colloidal dispersions and suspensions, the difference between a "good" and "bad" product is often determined by the absence or presence, respectively, of a very small, but significant, fraction of the sample mass, or volume, which lies above a particular diameter value. This small fraction of particle mass, or volume, is typically comprised of particles which are significantly larger than the mean diameter (expressed either as a number-weighted or volume-weighted average) of the overall PSD—indeed, often in a size range located several standard deviations above the mean diameter, comprising the outermost tail of the PSD, as discussed in connection with "A" and "B" in FIG. 3. It is frequently the case that the difference between a "good" and "bad" sample is effectively determined by differences in the fraction of the total particle volume (or mass) of less than 0.1%, and sometimes less than 0.01%.

This point is illustrated in FIG. 4A, which provides a simplified schematic picture of the differential, number-weighted particle size distributions for two samples which have very similar PSDs. The PSD for sample "B" has a large-particle "tail" which extends out a little further in diameter than the corresponding tail for sample "A". In this simplified case, "A" likely represents a "good" sample, while "B" represents a "bad" one. The additional amount of sample volume (mass) extending out to larger diameters in "B" may represent coalesced emulsion droplets, aggregated solid particles, insufficiently milled "primaries", etc., depending on the specific sample or application in question. Often, the performance and "quality" (however defined) of a final product made using sample "B" will be found to be deficient in at least one respect compared to the same product made using sample "A".

Such small differences in overall particle volume due to the existence of an additional (albeit very small) fraction of larger particles lying in the outermost tail of the PSD generally cannot be detected at all, let alone reproducibly and reliably, by various prior art "ensemble" techniques used for particle size analysis. These techniques are designed to yield an approximate PSD from a measurement in which the detected "signal" is generated by a very large number of particles—i.e. a representative fraction of the entire sample—at the same time. Such techniques include, but are not limited to, Fraunhofer ("laser") diffraction, Mie light scattering (often used in conjunction with the latter), and sedimentation (under gravity alone or aided by centrifugal force) using light or x-ray turbidimetry.

By contrast, the SPOS technique can be used to examine in detail the very small volume (or mass) fraction of particles which define the large-diameter tail of the PSD. It is often very useful to make a "partial PSD" measurement of the sample using a starting threshold diameter value $d_o$ (FIG. 4A) in the range of 0.5 to 2 microns, where the choice of $d_o$ depends on the PSD of the sample as well as the sensitivity (minimum detectable diameter), coincidence concentration limit and possibly other characteristics of the SPOS-type sensor used in the measurement. It is often the case that differences in sample quality which relate to relatively subtle differences in the large-diameter tail of the PSD, as illustrated in FIG. 4A, can be very easily and accurately resolved using the SPOS method of particle size analysis. In this case, the starting threshold diameter $d_o$ is typically located relatively far above the number-weighted mean diameter of the PSD. Only in this way is the PSA measurement maximally sensitive to small changes in the number, and hence the volume-fraction, of the "outlier" particles which ultimately determine the quality of the PSD and sample. This point is illustrated in FIG. 4B, which shows in magnified form the differences in the population PSDs assumed for samples "A" and "B", for particle diameters larger than $d_o$.

This situation is to be contrasted with that of FIG. 3, involving also the "slightly" different tails of PSDs "A" and "B". There is a significant difference between the ability to measure the tail portion of the PSD for samples "A" and "B" in FIG. 3, for $d \geq d_1$, and the ability to quantify the tail region for samples "A" and "B" in FIGS. 4A and B, for $d \geq d_o$. In the former case, one can easily raise the starting threshold diameter $d_1$ to a value much larger than the minimum detectable diameter $d_{MIN}$ of the SPOS sensor (and also the essential start of the PSD at $d_o$). In this way, one would seemingly be able to "exclude" the majority of particles comprising the PSD, smaller than $d_1$, so as to be able to increase the final particle concentration significantly and thereby increase greatly the number of particle counts in the tail region, $d \geq d_1$, thus improving the statistical accuracy of the partial PSD thereby obtained. However, any such improvement would likely be illusory. There would likely occur substantial, if not drastic, distortions in the partial PSD thereby obtained for $d \geq d_1$, as a result of the many coincidences of particles of smaller size, to which the SPOS sensor is sensitive. Hence, in practice it may be feasible to increase the concentration of the diluted sample suspension by only a relatively small extent, in order to improve the statistical accuracy of the partial PSD thereby obtained for $d \geq d_1$.

By contrast, in the case of samples "A" and "B" shown in FIGS. 4A and B, the great majority of particles in the sample are presumed to be smaller than the minimum lower size limit $d_{MIN}$ of the SPOS sensor utilized. The starting threshold diameter $d_o$ is then constrained by the requirement $d_o \geq d_{MIN}$. In this case, the effects of coincidences of particles smaller than $d_o$ on the accuracy of the partial PSD obtained for $d \geq d_o$ can be expected to be much less significant than the effects experienced for the examples discussed in connection with FIG. 3. In order to appreciate the difference between these two cases, it is useful to review briefly the response characteristics of a typical SPOS sensor.

For an SPOS sensor assumed to be operating in the traditional light-extinction (LE) mode and a particle diameter significantly larger than the wavelength of the light source (typically 0.7–0.8 $\mu$m), but smaller than the thickness of the active sensing zone, or "view volume" (typically 30–50 $\mu$m), the response of the sensor is approximately quadratic in particle diameter. That is, the height (voltage) of the pulse produced by a particle in the size range specified above passing through the active sensing zone increases with particle size approximately as the square of the particle diameter. This behavior has very significant and favorable consequences concerning the impact of particle coincidences on the measurement of the PSD for large-diameter tails, especially in the case shown in FIGS. 4A and B, where the great majority of particles lying below the starting threshold diameter $d_o$ are "invisible" to the sensor, on an individual basis. The quadratic response of an LE-type sensor means that the measurement of the very largest particles in a sample, which are present to a very small, and decreasing, extent above a sufficiently large diameter $d_1$ (FIG. 4), may be only slightly affected by the presence of a large number of significantly smaller particles occupying the active sensing zone of the sensor at the same time. In fact, in the case of particles smaller than approximately 2–3 microns, the dependence of pulse height on particle diameter is even stronger than quadratic, increasing to the 4th power, and eventually to the 6th power of the diameter, with decreasing particle size, because the extinction of light by a particle in an LE-type SPOS sensor is due increasingly to the phenomenon of light scattering, rather than geometric deflection (refraction). Hence, the accumulated effect of coincidences of particles of diminishing size may in many cases be negligible with respect to their influence on the measured pulse height for the "large" particles located in the outer tail of the PSD, notwithstanding the much larger number of smaller particles present in the diluted sample.

It should now be evident why automatic feedback control of a continuous, mixed-flow dilution system, based on monitoring of the particle count rate (or particle concentration, derived from the count rate using the known fluid flow rate) obtained from an SPOS-type sensor, is uniquely useful. For commonly encountered applications like the one discussed in general terms above and illustrated in FIGS. 4A and 4B, one often cannot know ahead of time, even approximately, what value of dilution factor DF should be employed. That is, even in the case of two samples which are judged to be nearly the "same", in terms of their average particle concentration and, possibly, other properties, the number, and therefore the volume-fraction, of particles lying above a given diameter threshold $d_o$ may vary greatly, even though the remaining portion (lower-diameter) of the PSD—indeed, the great majority of particles—is largely the same for the two samples. In such cases, an acceptable or optimal value of DF cannot be reliably estimated ahead of time, even given additional quantitative information (unrelated to particle size) about the sample suspensions.

The reason for this is that such additional information is generally influenced by the majority of particles comprising the PSD and hence, by definition, cannot reflect the relatively small differences in PSD which exist in the "tails" of the individual distributions. The information which might be available (i.e. measured), but is usually of limited value in predicting the desired DF value for a given sample, includes: 1) the total suspended particle mass (concentration); 2) the total suspended particle volume (concentration); 3) the turbidity (optical density) of the overall sample (suitably diluted by a constant factor); 4) the level of scattered light produced at some angle, or range of angles, by the overall sample (suitably diluted); 5) the total number of particles per unit volume of overall sample (too little influenced by the tiny fraction of large particles lying in the tail of the PSD); 6) the mean diameter (number- or volume-weighted) of the overall PSD, as determined by one or more ensemble techniques, such as laser (Fraunhofer) diffraction; 7) the standard deviation, or width, of the overall PSD, as determined by an ensemble technique.

Instead, the automatic dilution system described earlier can be used to determine an appropriate, or optimal, value for the dilution factor DF such that the particle concentration measured using a lower diameter threshold $d_o$ (i.e. for all $d \geq d_o$) lies below the coincidence concentration limit of the SPOS sensor. Whether the final concentration is adjusted by the system to be approximately equal to the coincidence limit, 80% of the latter, or 50%, 25% or even just 10% of the latter, depends on the extent to which the user is able to tolerate a moderate amount of distortion in the resulting partial PSD due to the effects of coincidences of particles smaller than $d_o$. The user may be able to tolerate only negligible distortion of the PSD by coincidences and therefore may opt for a final particle concentration which is only a fraction of the coincidence limit, as suggested above. The tradeoff, as noted earlier, is the level of statistical noise (going as the square root of the number of particle counts in a given diameter channel) in the measured PSD, which increases with decreasing particle concentration.

For a given application it may be useful to design the control algorithm for the automatic dilution system in a such a way that it makes a sequence of relatively short measurements, or "snapshots", of the partial PSD for $d \geq d_o$, where each measurement utilizes a different value for the desired final particle concentration (i.e. as determined from the particle count rate for $d \geq d_o$ and the fluid flow rate through the SPOS sensor). For example, at the start of the analysis the system might be designed to adjust the dilution factor DF so that the final particle concentration for $d \geq d_o$ is approximately equal to the coincidence concentration limit of the SPOS sensor. Particle count and size data would then be accumulated for a preset, relatively short period of time—i.e. long enough to achieve reasonable statistical accuracy in the resulting partial PSD. The system can then compute (and store in memory) the total particle volume contained in the measured PSD and the fraction that this volume represents of the total particle volume which passed through the sensor (i.e. including the majority of particles not measured, for $d<d_o$), obtained from the known injected volume of sample suspension (of known concentration) and the dilution factor DF. This quantity is the "volume fraction" contained in the measured partial PSD.

The system could then be designed to repeat this short measurement using a lower final particle concentration for $d \geq d_o$, perhaps equal to 50% of the nominal coincidence concentration limit of the SPOS sensor. If the resulting volume fraction of the partial PSD thus measured turns out to be appreciably smaller than that obtained using the prior value for the final "target" concentration (i.e. 100% of the coincidence limit), then the smart control system will conclude that the final particle concentration was too high (i.e. the dilution factor was too low), and therefore the measurement was adversely affected by particle coincidences. This sequence would then be repeated automatically, using yet a lower value for the final target concentration—e.g. another factor of two decrease, to 25% of the coincidence limit for the sensor. The system would determine once again the volume fraction for the partial PSD obtained using the new, lowered concentration. In this way, the smart control system can arrive easily and systematically at an acceptable, (approximate) maximum value for the final sample concentration, where distortion of the resulting PSD for $d \geq d_o$ due to particle coincidences is minimized, while the statistical accuracy of the resulting PSD is maximized. This would establish in an automatic fashion the "optimal" dilution factor DF and resulting final particle concentration for the dilute sample suspension.

In summation, for these "mostly-submicron" applications one must make a high-resolution measurement of a particular small portion of the PSD (i.e. $d \geq d_o$) in order to determine an optimal/appropriate value of the dilution factor DF to be used by the automatic dilution system, in order to make an accurate measurement of that limited part of the PSD.

As used hereinafter, "optimal dilution factor" and "optimal/appropriate value of the dilution factor" refer to the dilution factor value at which distortion of the PSD for $d \geq d_o$ due to particle coincidences in the SPOS sensor is minimized, or held to a predetermined, acceptable extent, while the statistical accuracy of the resulting PSD is maximized. The phrase "optimal particle concentration" refers to the particle concentration attained when an optimal dilution factor is utilized. It is to be understood that "minimized" and "maximized" as used herein are dependent upon the particular application or PSD for which the automatic dilution system of this invention is to be used and the characteristics of the particular SPOS sensor utilized. The system includes a CPU/Controller which is programmed to conduct a dialog with the user in order to determine from information provided by the user (e.g. by means of a software input menu) as to the SPOS sensor used and, for the particular application, as to the appropriate maximum acceptable particle concentration and the appropriate acceptable minimum statistical accuracy of the resulting PSD.

The principles of the present invention are implemented in several embodiments. In a first embodiment, a diluent delivery pump provides a flow of diluent fluid into a mixing chamber. A sample delivery pump injects a flow of concentrated sample suspension into the mixing chamber, where it is mixed with the diluent by an electromagnetically driven stirrer. The diluted sample suspension then flows through an SPOS sensor having an output from which the instantaneous particle count rate is obtained. From the count rate, circuit means provide a measurement of the maximum rate of increase of the particle concentration $R_{MAX}(0)$ indicating the rate of increase immediately after the start of injection of the concentrated sample suspension into the mixing chamber at a time which is much shorter than the time required for the particle concentration to reach equilibrium in the chamber. Computer means then computes from $R_{MAX}(0)$ the final particle concentration $C_0$/DF that would be achieved if one waited to ensure that the particle concentration in the diluted sample suspension had reached equilibrium.

The computed value of $C_0$/DF is compared with a desired optimal particle concentration for the SPOS sensor used, which concentration has been selected by the operator according to criteria as discussed above. From this comparison, a new value of DF needed to achieve the desired optimal output particle concentration is determined, and a new sample injection flow rate $F_S$ needed to achieve the new value of DF is computed. A control signal is then generated which controls the sample delivery pump to provide the new flow rate $F_S$. Concentrated sample suspension continues to be injected into the mixing chamber at the new flow rate $F_S$. After approximate equilibrium in the particle concentration in the fluid leaving the mixing chamber is reached, data are collected from the SPOS sensor, and a particle size analysis (PSA) is performed.

In order to reduce the residence time τ of the mixing chamber, a second embodiment may be used, in which the flow rates of diluent fluid and concentrated sample suspension are increased substantially, using values appropriate to achieve the desired dilution factor. In the second embodiment, instead of directing all of the diluted sample suspension through the SPOS sensor, only a portion of the diluted sample suspension in the mixing chamber is conveyed to the SPOS sensor through a flow tube having its input end positioned in the mixing chamber. The flow of the diluted sample suspension through the flow tube is assisted by a diluted sample metering pump which may be positioned either before or after the SPOS sensor. The rest of the diluted sample suspension which exits the mixing chamber flows from the latter to a drain.

A third embodiment is typically able to provide a reduction of the time needed for the dilution system to reach equilibrium after a change in the flow rate of the sample suspension or the diluent fluid. In the third embodiment the stirred mixing chamber is replaced by a "static" mixer of smaller effective volume. The concentrated sample suspension is drawn through pumping means and is injected into the flow tube for the diluent fluid, with a static mixer located downstream from the point of injection of the sample suspension. Since the static mixer is typically no larger in diameter than the diluent flow tube, the effective volume of the mixer may be greatly reduced when compared with the typical volume of the stirred mixing chambers of the first two embodiments. Because the effective volume of the stirred mixing chamber may be greatly reduced, there may be a significant reduction in the residence time τ. Accordingly, only a relatively short time is needed for the output particle concentration to reach steady-state equilibrium after the injection flow rate of either the sample suspension or diluent fluid is changed. Because the dilution factor DF can therefore be adjusted almost instantaneously, the automatic control system more closely resembles a system with conventional negative feedback control.

Because some kinds of sample suspensions may be damaged (i.e. their PSDs altered) by coming into contact with pumping means, a modification of the third embodiment provides means to physically isolate the concentrated sample suspension from the pumping means. A pair of valves controls filling of a capture reservoir, which may simply be a length of tubing, with the sample suspension. The pumping means then pumps diluent into one end of the capture reservoir in order to force the sample suspension from the opposite end of the capture reservoir so as to be injected directly into the flow tube for the diluent fluid, immediately upstream of the static mixer.

A two-stage dilution system is employed in a fourth embodiment. The concentrated sample suspension is injected along with diluent fluid into a first predilution mixing chamber which is caused to be emptied in a controlled fashion into a second mixing chamber. A quantity of prediluted sample suspension in the first mixing chamber is forced to flow continuously into the second mixing chamber by injecting additional diluent fluid into the first mixing chamber at an adjustable flow rate. Diluent fluid is injected continuously, typically at a fixed flow rate, into the second mixing chamber to further dilute the prediluted sample suspension in steady-state fashion. This two-stage dilution technique can in principle achieve much larger values of the overall dilution factor DF than is possible with a single-stage arrangement.

The most useful features of the third and fourth embodiments are combined in a fifth and preferred embodiment. From the fourth embodiment, the fifth embodiment incorporates the concept that by using a two-stage dilution process the extent of the dilution can be greatly increased. Thus, the fifth embodiment uses a predilution chamber for prediluting the sample suspension with a diluent fluid. However, rather than use a second stirred mixing chamber as the second stage, the fifth embodiment employs the concept of reducing the time needed to reach equilibrium used in the third embodiment—that is, it uses a static mixer of small effective volume in the second dilution stage. Diluent fluid flows in a tube and the prediluted sample suspension from the first mixing chamber is injected into the tube upstream of the static mixer. Thus, the fifth embodiment has the advantages of a potentially large dilution factor due to two stages of dilution and a relatively short time to reach equilibrium afforded by the use of a relatively small volume mixing device—the static mixer.

A variant of the fifth embodiment provides an additional (non-SPOS) sensing device for the doubly-diluted sample suspension. Valves control the flow of the doubly-diluted sample suspension sequentially into a first branch from the static mixer through the SPOS sensor or a second branch into a dynamic light scattering (DLS) cell, for the purpose of providing an overview of the PSD of all the particles in the sample suspension, assuming that the overall PSD is mostly submicron and therefore suitable for a DLS measurement. Because the DLS technique requires that the diluted sample suspension be stationary, the diluted sample suspension is held for a time in the DLS cell while light scattering data are collected and suitably processed to yield a computed PSD.

DESCRIPTION OF THE PREFERRED EMBODIMENTS

Figure 5:
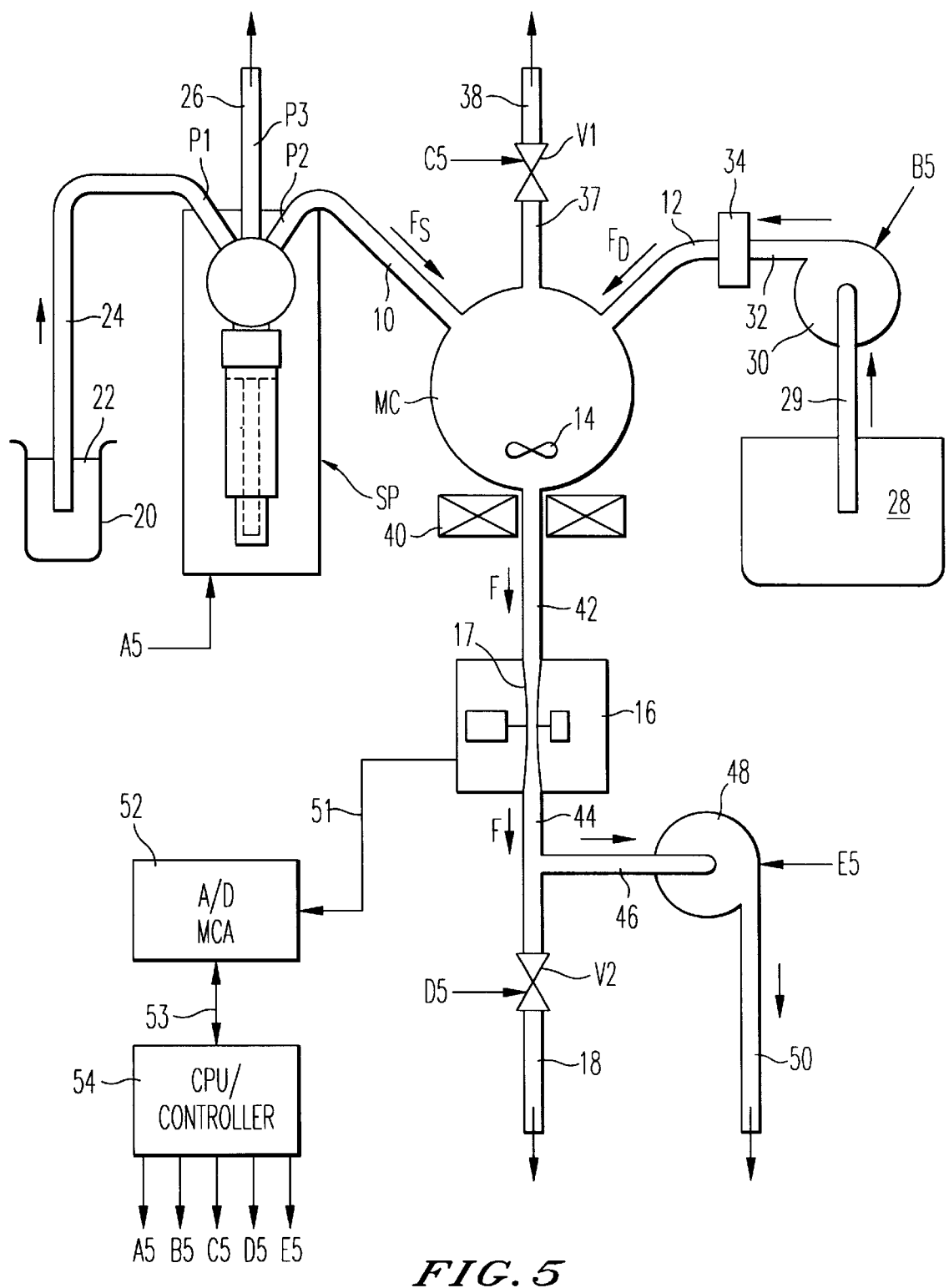
FIG. 5 is a diagram of a first embodiment of an automatic dilution system of the invention.

A simplified schematic diagram of a first embodiment of the invention is shown in FIG. 5. This embodiment represents perhaps the simplest and most straightforward realization of the continuous, mixed-flow method discussed above. Fresh diluent fluid is pulled through inlet tube 29 from a holding tank 28 or supply pipe by a suitable delivery means 30, such as a variable-speed pump, and transmitted through an output tube 32, optionally through a filter 34, and tube 12 to a mixing chamber MC. The rate of flow of the diluent fluid $F_D$ is adjusted to a desired value by varying the output flow rate of delivery pump 30 in response to a control signal B5, generated by a CPU/Controller 54.

Separately, a quantity of starting concentrated sample (particle) suspension 22, available in container 20 (e.g. a beaker, holding tank or supply pipe), is injected at a desired flow rate $F_S$ into mixing chamber MC by a suitable delivery means. In the example shown in FIG. 5 the delivery means is a syringe pump SP. At the start of the dilution process a control signal A5, generated by CPU/Controller 54, instructs syringe pump SP to pull a quantity of concentrated sample suspension 20 into a syringe at a suitable flow rate through the inlet tubing 24 and input port P1. Syringe pump SP is then commanded by control signal A5 to inject the captured concentrated particle suspension into mixing chamber MC via output port P2 and tubing 10 at the desired flow rate $F_S$. The value of flow rate $F_S$ is chosen according to the desired value of the dilution factor DF, as described earlier (and further below). At the conclusion of the measurement, any excess sample suspension which remains in syringe pump SP, plus the quantity located in tubing 24 between sample source 22 and input port P1, can be pumped through the output port P3 and tubing 26 to a drain (or recirculated back to the starting source) by syringe pump SP in response to control signal A5.

The concentrated sample suspension and fresh diluent fluid which are caused to flow continuously into mixing chamber MC are stirred, typically using either an adjustable-speed electromagnetic stirrer comprising winding 40 plus associated circuit means and magnetic stir bar 14, as shown in FIG. 5, or, alternatively, a mechanical stirrer (motor, shaft and propeller). Ideally, the stirring apparatus is designed so that mixing of the fluid/particle contents of mixing chamber MC is carried out in an efficient, random fashion, resulting in the particle concentration (expressed either as the number of particles of all sizes, or the number in any given size range, per unit volume of fluid suspension) being approximately uniform throughout mixing chamber MC at any given time. Owing to conservation of fluid volume, the diluted particle suspension which exits mixing chamber MC via output port 42 has a flow rate F equal to the sum of the individual flow rates $F_S$ and $F_D$ (Equation 1), once a condition of flow (pressure) equilibrium has been reached in mixing chamber MC. This diluted suspension passes directly through an SPOS-type sensor 16 and tubing 44 to a drain via tubing 18, optionally through valve V2, which can be actuated electrically or pneumatically by a control signal D5, generated by CPU/Controller 54.

As shown in FIG. 5, there is an additional output port 37 from mixing chamber MC connected to a drain via tube 38 through "bleed" valve V1, which is actuated by a control signal C5, generated by CPU/Controller 54. This permits mixing chamber MC to be optionally purged of residual air at the start of the dilution process. Fresh diluent fluid is pumped into mixing chamber MC, either at the usual prescribed flow rate $F_D$, or at a conveniently faster rate, with valve V1 open, until mixing chamber MC is completely filled with fresh diluent fluid, with excess diluent being allowed to pass to a drain via tube 38 through valve V1. Valve V1 is then closed, permitting the mixed-flow sample dilution process to begin. In an alternative mode of operation, diluent fluid is pumped into an empty mixing chamber MC with valve V1 open until mixing chamber MC contains a predetermined volume V of fluid, where V is smaller than the physical internal volume of mixing chamber MC. Valve V1 is then closed so that an air space resides over the fluid volume V in mixing chamber MC. The dilution process can then commence in the usual way.

An "assisted-drain" pump 48, or other fluid delivery means, can be used optionally to bypass valve V2 and directly pull the diluted sample suspension and/or fresh diluent fluid supplied by delivery means 30, perhaps at a flow rate higher than $F_D$, from mixing chamber MC and through SPOS sensor 16, tubing 44 and tubing 46 to a drain via tubing 50 after a measurement is completed. The optional pump 48 may be useful for quickly emptying mixing chamber MC (with valve V1 open) and flushing mixing chamber MC with fresh diluent fluid between successive sample dilutions and measurements.

As discussed earlier, for applications requiring relatively large dilution factors DF, the sample flow rate $F_S$ will be much smaller than the diluent flow rate $F_D$. In such cases, the flow rate F of fluid exiting mixing chamber MC via tube 42 and passing through SPOS sensor 16 will be approximately equal to $F_D$. One must recognize the fact that an SPOS-type sensor exhibits optimal sensitivity and resolution over only a relatively limited range of fluid flow rates. Any significant increase in the total flow rate of fluid passing through the sensor can be expected, in general, to reduce significantly its performance and, hence, the resulting effectiveness of any particle size analyzer based on the SPOS method which utilizes such a dilution system—assuming that the entire fluid stream which exiting mixing chamber MC is made to pass through the SPOS sensor. An alternative embodiment of this invention, described below, bypasses this requirement.

In general it is usually advisable to hold the diluent flow rate $F_D$ constant, choosing a value which is appropriate or optimal for the particular SPOS sensor being utilized. The sample suspension injection flow rate $F_S$ is then varied by the control system in order to adjust the dilution factor DF (Equation 2) to the appropriate or optimal value for the PSA measurement in question. The diluent fluid flow rate can be adjusted to the desired value through the use of an appropriate control signal B5, generated by CPU/Controller 54.

Figure 1:
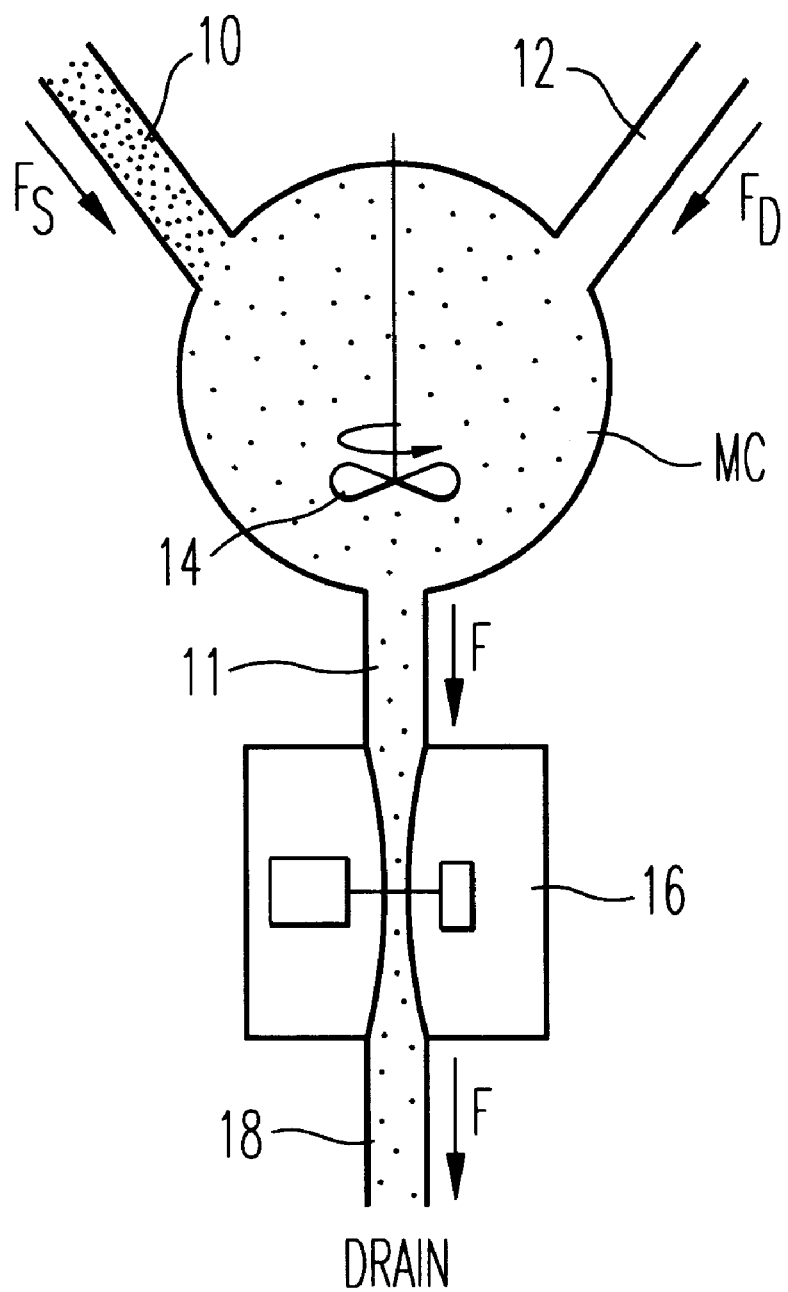
FIG. 1 is a simplified diagram of a prior art "mixed-flow" system for diluting a concentrated sample fluid.
Figure 2:
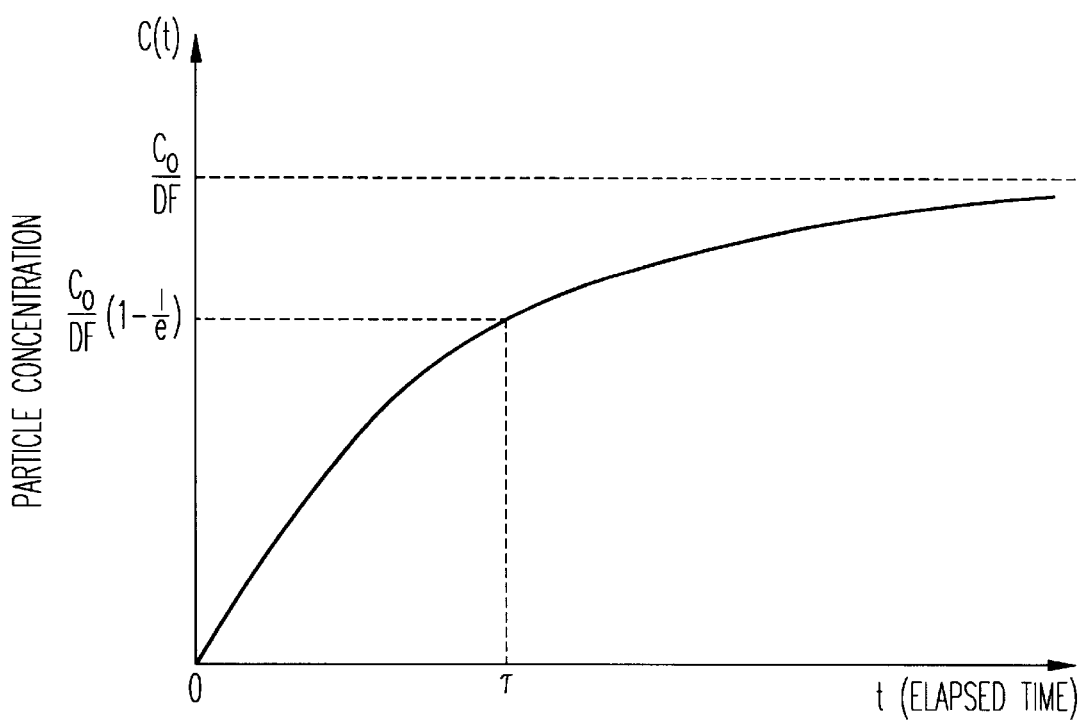
FIG. 2,is a plot showing the relationship of particle concentration and elapsed time in the system of FIG. 1.
Figure 3:
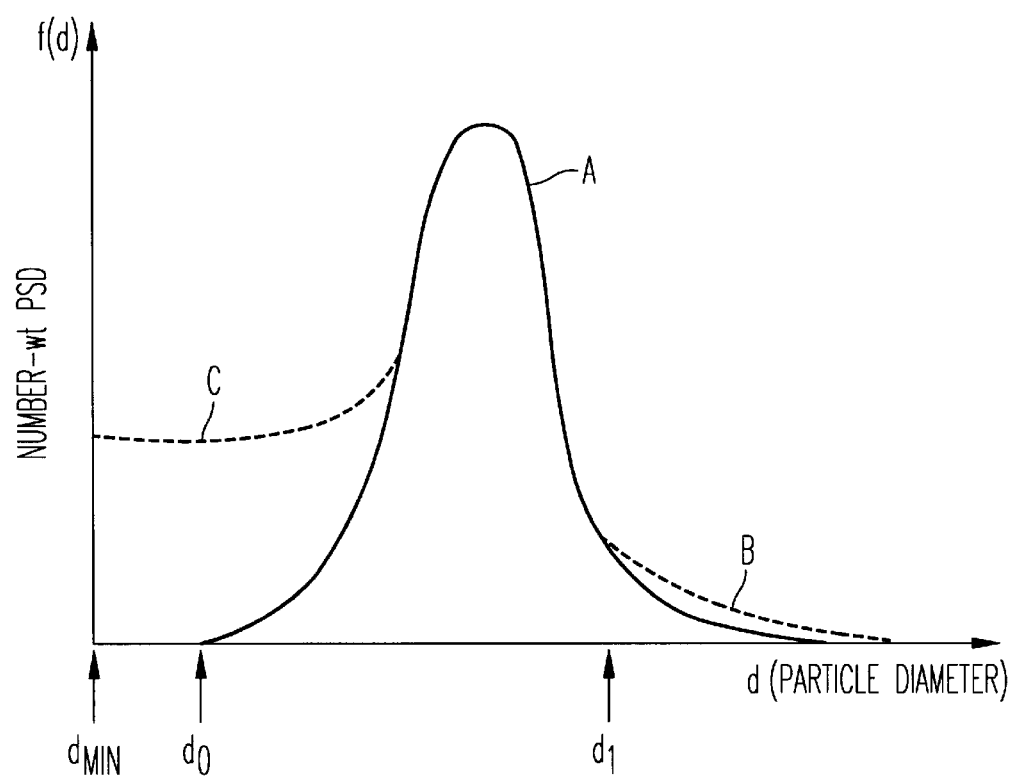
FIG. 3 is a plot illustrating three particle size distributions (PSDs) obtained from typical samples.
Figure 4A:
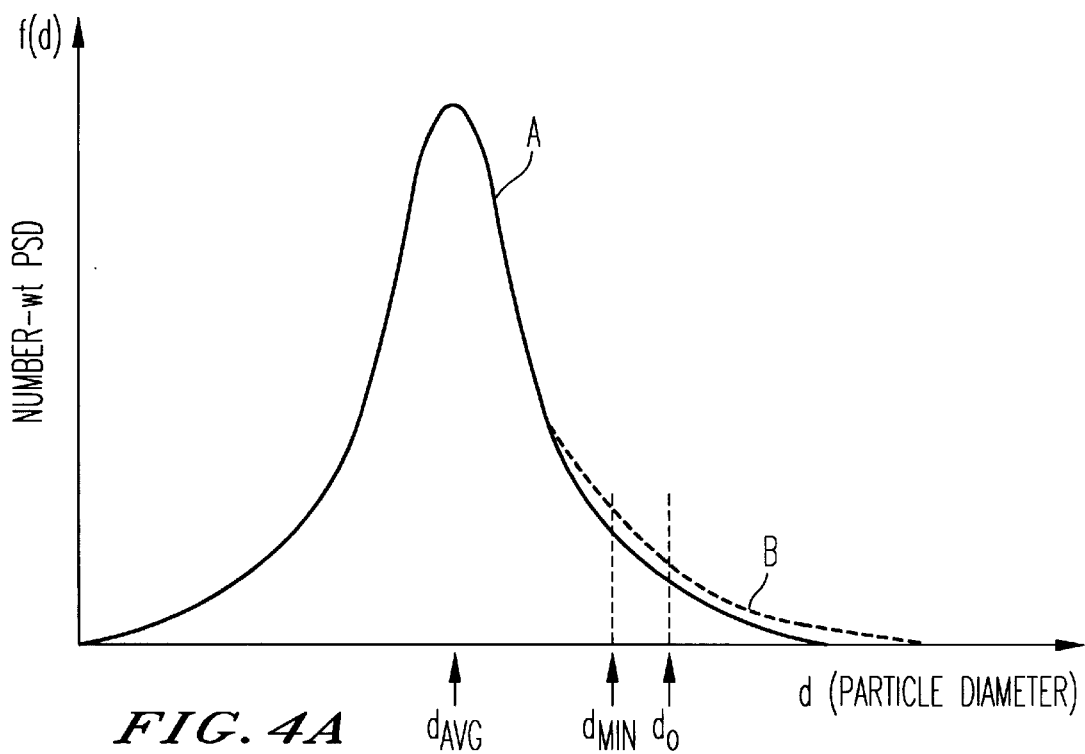
FIGS. 4A and 4B are plots providing a picture of the differential, number-weighted PSDs for two similar samples.
Figure 4B:
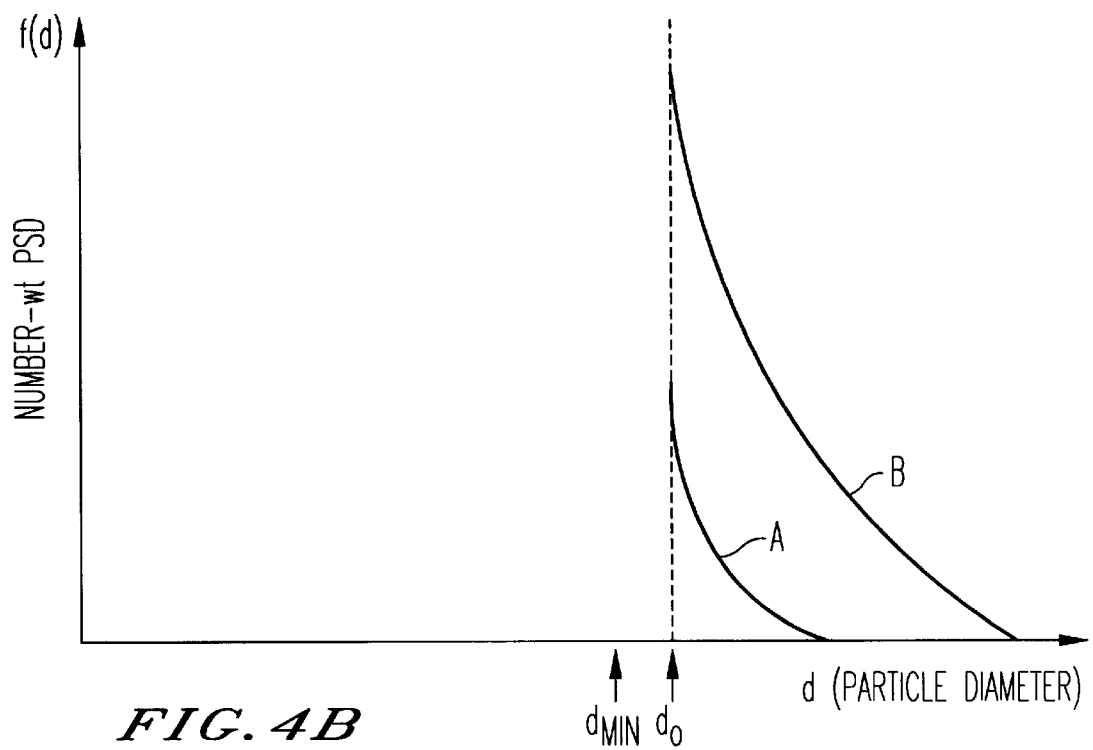

In a typical realization of this embodiment, utilizing a combined light-extinction and light-scattering SPOS-type sensor designed to count and size particles in the diameter range (nom.) 0.5 to 400 microns, it is convenient to fix the diluent flow rate $F_D$ at 1 ml/sec. Frequently, one wishes to use such an automatic dilution apparatus in conjunction with a PSA instrument for applications requiring determination of the absolute fraction of the total volume, or mass, of the dispersed particle phase in a given range of particle diameters, as was discussed above in connection with FIGS. 4A and B. In such cases, this fraction, which can be calculated from the measured PSD, will be in error to the same extent that the computed value of DF is in error. Because the dilution factor DF depends on the ratio $F_D/F_S$, as indicated by Equation 2, any uncertainty in the value of $F_D$ will directly result in an uncertainty in the value of DF. Accordingly, depending on the type and quality of the diluent delivery pump utilized, it may be necessary or advisable to install a flow gauge (e.g. with an electronic output signal) between delivery pump 30 and mixing chamber MC, so that the flow rate $F_D$ can be monitored and adjusted to the desired value, either manually or by automatic means, including the use of the principle of negative feedback, using an output signal derived from the flow gauge to control the output flow rate of diluent delivery pump 30.

It should be appreciated that programmable, adjustable-speed syringe pump SP is only one of several possible means for delivering concentrated sample suspension at a given, adjustable flow rate $F_S$ to mixing chamber MC. Alternative devices which can be used to implement this critical function include, but are not limited to: peristaltic pump (driven by an adjustable-speed, variable-voltage d.c. motor or digitally-controlled stepper motor), an adjustable-speed gear pump and an adjustable-output "metering" pump. Regardless of the type of pump or fluid metering device which is chosen to implement this function, it should be able to provide a reasonably steady output flow of concentrated sample suspension, with the flow rate adjustable by electronic (or pneumatic) means over a wide dynamic range. Use of a syringe pump is appropriate for applications requiring very accurate, reproducible metering of the concentrated sample suspension, possibly requiring a large dynamic range of output flow rates.

For example, syringe pumps are available which can vary the time of injection from a few seconds to 600 sec, or even longer, with very small, "micro" steps in incremental delivered volume available using a stepper-motor drive mechanism. As an example, if one uses a 1-ml syringe with such a programmable syringe pump, then total injection times in the range of, say, 5 to 500 sec translate into a range of flow rates $F_S$ of 0.2 to 0.002 ml/sec, respectively. If one further assumes a fixed diluent flow rate $F_D$ equal to 1 ml/sec, then the values above translate into a range of dilution factors DF of 6 to 501, respectively—i.e. a dynamic range of 83.5:1. In the former case, the flow rate F of the diluted sample suspension exiting mixing chamber MC and passing through the sensor will be 1.2 ml/sec, while the rate in the latter case will be 1.002 ml/sec. This variation of about 20% in the flow rate F is sufficiently small on a percentage basis that it typically will not result in any significant variation in the amplitudes of the pulses comprising the analog output signal of SPOS sensor 16 for a given particle size. That is, the sensor response, or "calibration curve", of pulse height (voltage) vs particle diameter should change only minimally over the above range of flow rates F.

An essential element of this invention, in general, and of the design of this first embodiment (and subsequent embodiments discussed below), in particular, is the use of a control signal to adjust the output flow rate $F_S$ of syringe pump SP—both at the outset of the dilution and PSA measurement process and also, optionally, in "real time" thereafter. The relevant control signal A5 can be regarded as providing a type of "negative feedback" control. Typically, it consists of a set of digital values, delivered either in serial or parallel format by CPU/Controller electronic subsystem 54. Alternatively, signal A5 might consist of a varying analog voltage or current, depending on the requirements of syringe pump SP or other sample delivery means. In accordance with the description above, this control signal, which determines the output flow rate $F_S$ of the sample delivery subsystem—in this case programmable syringe pump SP—is derived from a measurement of the particle count rate, or equivalently, the particle concentration per unit volume of fluid flowing through SPOS sensor 16.

The instantaneous particle count rate (pulses/sec) can be obtained by simple, well-known electronic means directly from the output signal of the SPOS-type sensor, which typically consists of individual, isolated pulses of varying height (peak voltage), superimposed on a "baseline" voltage level (ideally close to zero). The pulse height ideally increases monotonically with increasing particle diameter. For the purpose of determining an appropriate or optimal value for the dilution factor DF, the particle count rate is often taken to be the number of pulses per second for pulse amplitudes higher than a preset "threshold" value, corresponding to a given minimum particle diameter. It can also be derived from the number of pulses per second but only for those pulses having amplitudes higher than a given first threshold value and smaller than a given second threshold value, corresponding only to those particles lying within a given, selected range of particle diameters. The corresponding particle concentration (again, either for all particles larger than a given threshold diameter or only for those particles in a given size range) can be obtained from the appropriate particle count rate by dividing the particle count rate by the fluid flow rate F. This calculation can be made using the CPU/Controller subsystem 54 or a central controller computer. This value of particle concentration can then be used to generate an appropriate control signal (A5 in FIG. 5), to raise or lower the volumetric rate of injection $F_S$ of concentrated sample suspension into mixing chamber MC, thus decreasing or increasing, respectively, the dilution factor DF, in order to achieve a particle concentration which is optimal for the SPOS-type sensor being utilized, as defined previously.

Once steady-state equilibrium has been reached for the particle concentration residing in, and exiting from, mixing chamber MC (after a time of approx. $3\tau$ has elapsed, where $\tau = V/F$) and the PSA measurement starts, the total integrated particle volume, or mass, which passes through SPOS sensor 16 is ideally the same as that which has been pumped or injected by syringe pump SP into mixing chamber MC. As an example, one can assume a starting oil-in-water emulsion, in which the oil phase (consisting of individual droplets) comprises 20% of the volume of the suspension (i.e. 0.2 ml/ml). One can further assume that the automatic dilution system has arrived at an optimal dilution factor DF of 241 (with $F_D$=1 ml/sec, or 60 ml/min and $F_S$=0.25 ml/min) and that, after equilibration, the total elapsed time of the PSA measurement is two minutes. These assumptions therefore imply that the volume of starting sample suspension delivered to mixing chamber MC and thus passing through SPOS sensor 16 equals 0.5 ml, of which 0.1 ml is the total volume of the oil phase (droplets) passing through the sensor.

To the extent that one wishes to achieve a rapid dilution of the starting concentrated sample suspension, one should in general design a continuous dilution apparatus having the shortest practical residence time $\tau$. From Equation 4 it is clear that this preference implies selection of either a small volume V for the mixing chamber, or a large total fluid flow rate F, or both. The second condition effectively implies a large flow rate of diluent $F_D$ because in most cases of practical interest, as indicated above, $F_D$ will be considerably larger than $F_S$, assuming that a relatively large value of DF is required. However, the value of DF itself depends on the value of $F_D$, as described by Equation 2. Hence, in practice in order to shorten $\tau$ one generally chooses to keep the flow rate $F_D$ constant and, instead, to reduce the volume V of mixing chamber MC. Also, it is generally undesirable to increase the total flow rate F (as a consequence of increasing the flow rate of diluent fluid $F_D$) of diluted particle suspension exiting mixing chamber MC and passing through SPOS sensor 16, in order to decrease the residence time $\tau$ of the chamber.

There is a potentially significant disadvantage in choosing too small a value for mixing chamber MC volume V—namely, the risk of causing unacceptably large fluctuations in particle concentration in the fluid stream exiting mixing chamber MC. Such fluctuations can result from insufficient mixing of the fresh diluent and concentrated sample fluids as they enter the very small mixing chamber volume. In any case, it is often difficult to achieve ideal mixing of the fluid contents of mixing chamber MC. Relevant parameters which influence the quality of the mixing process include, but are not limited to: volume and shape of the mixing chamber; speed of stirring; shape of the stirring element; inclusion/design of an off-axis "spoiler", used to induce turbulent, chaotic mixing; design and positioning of the ports/injectors for the two input fluids; and the design and positioning of the port for the output fluid stream.

Therefore, in order to minimize the magnitude of fluctuations in the particle concentration in the diluted sample fluid stream exiting mixing chamber MC, one should in general increase the volume V of mixing chamber MC, so as to "dampen" the unwanted fluctuations. However, one must obviously also avoid choosing too large a volume V for mixing chamber MC. The larger the value of V, the longer the residence time $\tau$, assuming that the total fluid flow rate F cannot be increased correspondingly, typically due to constraints imposed by the SPOS-type sensor. Hence, the larger the volume V the longer will be the time needed to reach equilibrium in the particle concentration of the fluid stream exiting the mixing chamber and entering the sensor.

In addition, there is another disadvantage associated with choosing too large a value for volume V. Following analysis of a given sample, mixing chamber MC needs to be flushed with diluent fluid to eliminate most of the existing sample particles, thereby reducing the risk of significant cross contamination of the next sample. The flushing process involves passing clean diluent fluid into mixing chamber MC for a prolonged period of time—again, typically at least $3\tau$—so that a negligible number of "old" particles remain in mixing chamber MC. Of course, time $\tau$ can be decreased by momentarily increasing the flow rate $F_D$ of diluent fluid entering mixing chamber MC during the flushing process. However, notwithstanding this factor, it remains desirable to avoid an excessively large volume for mixing chamber MC, all other factors being equal. In summary, choice of an optimal value for volume V can be made only by trading off the two opposing demands. Modifications in the design of the dilution system will be discussed below, in connection with alternative embodiments of the invention.

For applications involving particle size analysis using the SPOS method, one typically wishes to utilize a fluid flow rate F through the sensor in the range of 25–100 ml/min. For example, it is often convenient to utilize a sensor flow rate of 60 ml/min, i.e. 1 ml/sec. In this case, a good choice for volume V for a stirred mixing chamber lies in the range of 10–25 ml, resulting in a corresponding residence time $\tau$ of 10–25 sec. Assuming that an elapsed time of $3\tau$ is chosen to reach essential equilibrium and stable particle concentration before commencing data acquisition, the corresponding waiting time would be 30–75 sec.

It is useful to summarize the steps which comprise a typical cycle of operation of an automatic dilution system designed according to the first embodiment of the invention as shown in FIG. 5:

1. At the start of system initialization, drain valve V2 remains closed (and optional drain/flush pump 48 off) and "bleed" valve V1 is opened, by means of control signal C5. Mixing chamber MC is filled with fresh diluent fluid by energizing diluent delivery pump 30, by means of control signal B5, for a sufficient period of time, based on the flow rate $F_D$ and the desired working volume V of fluid in mixing chamber MC. Excess diluent fluid is allowed to flow to a drain through valve V1. Diluent delivery pump 30 is then turned off by means of control signal B5 and valve V1 is closed by means of control signal C5. Initialization (i.e. filling) of mixing chamber MC is now complete.

2. Flushing/cleaning of mixing chamber MC and sensor 16 is accomplished by opening drain valve V2 by means of control signal D5 and energizing diluent delivery pump 30 by means of control signal B5. Signal B5 is also used to adjust the output flow rate of diluent delivery means 30 to a value appropriate for flushing the system, which optionally may exceed the desired flow rate $F_D$ for sample dilution and the PSA measurement. The approximate particle concentration in the fluid exiting mixing chamber MC is determined by monitoring the pulse rate of the output signal of SPOS sensor 16 during the flushing process in order to identify an "end point" for automatic termination of the flushing process when the background particle concentration has fallen below an acceptable, preset level.

3. Next, the sample capture and delivery subsystem is initialized. The syringe in syringe pump SP is filled with fresh sample suspension 22 via tubing 24, as instructed by control signal A5. Syringe pump SP is then instructed by control signal A5 to inject a quantity of the sample suspension into tubing 10, so that it becomes filled, or "primed".

4. The system commences automatic dilution of the starting sample. Drain valve V2 is opened, by means of control signal D5. Delivery of diluent fluid into mixing chamber MC at the desired, fixed flow rate $F_D$ is begun by energizing diluent delivery pump 30, using control signal B5. Injection of concentrated sample suspension into mixing chamber MC is initiated by syringe pump SP, under command of control signal A5. This action permits mixing of the diluent fluid and sample suspension and dilution of the sample suspension in mixing chamber MC, establishing a specific starting ("trial") value for the dilution factor DF equal to $1+F_D/F_S$.

5. The initial (i.e. maximum) rate of increase of the particle concentration, $R_{MAX}(0)$, in the dilute sample suspension exiting mixing chamber MC and flowing through SPOS sensor 16 is measured at the start of the dilution process. From this value the approximate expected value of the equilibrium concentration $C_0/DF$ is calculated (Equation 8) in CPU/Controller 54.

6. The calculated value of $C_0/DF$ is compared in CPU/Controller 54 with the optimal desired particle concentration for the SPOS sensor utilized, provided by the operator at the outset the automatic dilution and PSA process by suitable input means, based on the coincidence concentration limit of the SPOS sensor and/or the detailed structure of the PSD for the sample application in question, as discussed previously. Based on this comparison, a new value of DF which is needed to achieve the desired particle concentration is determined in CPU/Controller 54. The new sample injection flow rate $F_S$ which is needed to achieve this desired value of DF is computed in CPU/Controller 54. The appropriate control signal A5 required to instruct syringe pump SP to adopt the new output flow rate $F_S$ is transmitted to syringe pump SP from CPU/Controller 54.

7. Concentrated sample and fresh diluent continue being injected into mixing chamber MC at their respective flow rates $F_S$(new) and $F_D$. A delay time of approximately $3\tau$ is allowed to elapse in order to achieve essential equilibrium in the particle concentration in the fluid exiting mixing chamber MC and passing through SPOS sensor 16.

8. Data are collected from SPOS sensor 16 and the PSD is constructed in CPU/Controller 54 or an external computer over the desired range of particle diameters for a time sufficiently long to achieve the desired level of statistical accuracy in the diameter "channel" data comprising the population PSD.

9. Mixing chamber MC is flushed with fresh diluent fluid (see #2 above) until the particle concentration falls below an acceptable, preset level, thus preparing the system for another dilution/measurement cycle.

As indicated in the discussion above, it is advantageous to reduce the residence, or settling, time $\tau$ of the mixing chamber MC in order to achieve faster equilibrium in the mixed-flow dilution process, thereby reducing the overall time needed for an effective PSA measurement. It is also pointed out that, in principle, this goal can be accomplished either by decreasing the fluid volume V in mixing chamber MC, or increasing the combined flow rate F of the fluid entering and leaving mixing chamber MC, or both. Implementation of the first change will be discussed subsequently. However, at this point it is worth considering the improvement which can be made in the response time $\tau$ of the dilution system by increasing the rate of fluid flow F.

Figure 6A:
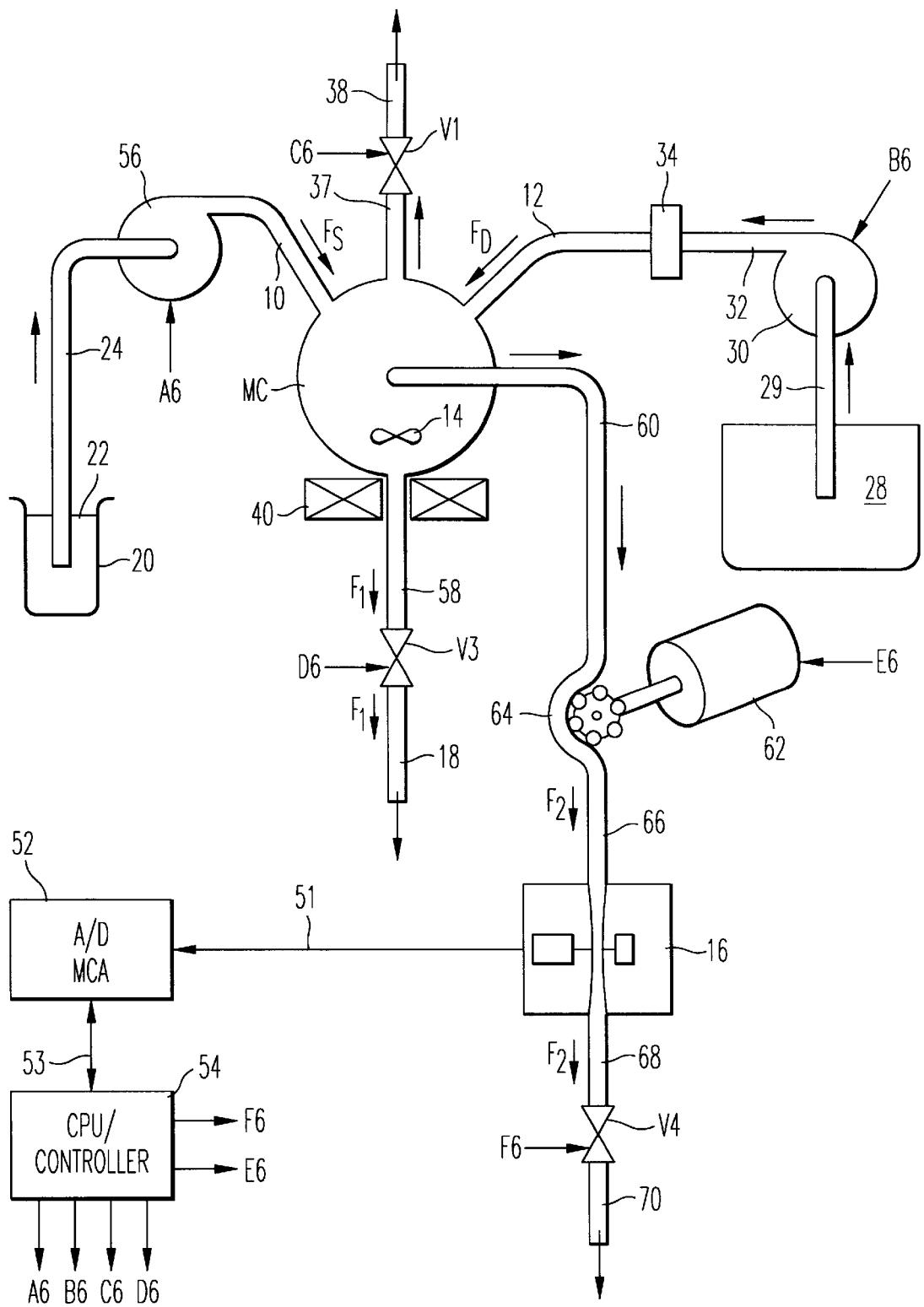
FIG. 6A is a diagram of a second embodiment of an automatic dilution system of the invention.

A simple variation in the fluidics design of the first embodiment of FIG. 5 forms the basis for the second embodiment of the invention, shown schematically in FIG. 6A. As is evident, the design of the fluidics system shown in FIG. 6A bears a strong resemblance to that used in the first embodiment of FIG. 5. Like the first embodiment, the embodiment of FIG. 6A uses a stirred mixing chamber MC and independent, controllable means for delivering fresh diluent fluid and concentrated sample suspension to the mixing chamber MC at the respective flow rates $F_D$ and $F_S$ in order to achieve a variable dilution of the sample suspension. As before, the dilution factor DF at equilibrium is given by $1+F_D/F_S$. However, at this point the fluidics designs of the two embodiments diverge markedly.

In the second embodiment of FIG. 6A, the fluid exiting mixing chamber MC at flow rate $F_1$, in equilibrium with the two input flow rates $F_D$ and $F_S$, no longer passes through the sensor. Rather, it goes directly to a drain via tubing 58 and tubing 18, optionally through a drain valve V3, actuated by a control signal D6 generated by CPU/Controller 54. The sensor "captures" a quantity of diluted sample suspension directly from the internal fluid contents of mixing chamber MC. A separate delivery means, shown schematically as a peristaltic-type pump 62 including a curved section of tubing 64, is used to pull diluted sample suspension through tubing 60 from the mixing chamber MC and deliver it continuously at a desired flow rate $F_2$ through tubing section 66 to SPOS-type sensor 16. This diluted sample suspension then flows to a drain, via tubing 68 and tubing 70, optionally through a drain valve V4, actuated by a control signal F6 generated by CPU/Controller 54.

This apparently small change in design results in a significant change in the operation of the dilution system shown in FIG. 6A. In essence, the mixed-flow dilution process has now been "decoupled" from the function of passing diluted sample suspension through the SPOS-type sensor. As a result, flow rates $F_1$ and $F_2$ need not be the same. Hence, it is now possible to select an optimal value for $F_2$ based on the characteristics and requirements of the sensor, completely independently of the choices for the injection flow rates $F_D$ and $F_S$, which influence not only the dilution factor DF but also the residence time $\tau$ of the mixing chamber MC.

As should be readily apparent, the consequence of the decoupling of flow rates $F_1$ and $F_2$ is important. Relatively large values can now be chosen for $F_D$ and $F_S$ without regard for the flow requirements of the sensor, in order to achieve a relatively large value for the total fluid flow rate into and out of mixing chamber MC. The value of DF is still adjusted by changing $F_S$ (or $F_D$), as before. However, one can now achieve a relatively short residence time $\tau$ for mixing chamber MC given by $V/F_1$. This result, in turn, has the valuable consequence of speeding up the response time of the dilution system—i.e. shortening the time needed for the system to reach steady-state equilibrium and an essentially fixed particle concentration within mixing chamber MC following adjustment of the DF value (e.g. through a change in $F_S$) by the automatic control system, allowing a reliable, reproducible PSA measurement to be made.

In principle, one can thus achieve a relatively short residence time $\tau$ without having to reduce the volume V of the mixing chamber simply by increasing the rate of fluid flow into and out of the mixing chamber. As long as both $F_D$ and $F_S$ are "scaled up" by the same factor, above the values they would have using a design like that of the first embodiment of FIG. 5 (in which the fluid output of the mixing chamber passes directly through the sensor), the resulting value of DF will remain the same. However, the dilution system will achieve equilibrium more quickly—i.e. by the same factor used to increase $F_D$ and $F_S$.

A numerical example is useful. In the first embodiment of FIG. 5, one can choose V=25 ml, $F_D$=1 ml/sec and DF=100, requiring a sample injection flow rate $F_S \approx 0.01$ ml/sec. The resulting fluid flow rate into and out of mixing chamber MC (and sensor 16) is $F \approx 1.01$ ml/sec, and the residence time $\tau$ equals $V/F \approx 25/1.01 \approx 24.8$ sec. For the second embodiment of FIG. 6A, one may start by assuming that the injected fluid flow rates have been scaled up by a factor of 10, with the volume of the mixing chamber kept the same. This assumption results in $F_D$=10 ml/sec and $F_S \approx 0.1$ ml/sec. The resulting flow rate through mixing chamber MC is $F_1 \approx 10.1$ ml/sec, and the residence time $\tau$ becomes $V/F_1 \approx 25/10.1 \approx 2.48$ sec, a factor of 10 decrease. Meanwhile, the value for DF is the same (100). Further increases in the values of $F_D$ and $F_S$ result in a corresponding decrease in $\tau$ with DF unchanged.

Operation of an automatic dilution system based on this second embodiment of FIG. 6A would essentially be the same as that described earlier for the first embodiment of FIG. 5. The output of SPOS sensor 16, suitably processed by an A/D (analog-to-digital) converter and MCA (multichannel analyzer) electronic circuit 52 and associated CPU (central processor unit)/Controller 54, yields a value for the particle count rate (# particles/sec). Together with the known value of the flow rate $F_2$, this yields a corresponding particle concentration (# particles/ml), either for the entire measurable particle size range or over a selected segment thereof. Based on the coincidence concentration limit of SPOS sensor 16 as well as the "optimal" concentration for the specific particle sizing application of interest (as discussed earlier), this information can be used to generate a real-time control signal A6, which is used to control the sample delivery means 56 and thereby adjust the flow rate $F_S$ of injection of concentrated sample suspension into mixing chamber MC.

Owing to this significant reduction in the residence time $\tau$ of the mixing chamber achieved by the use of appropriately higher flow rates $F_D$ and $F_S$, as explained above, it is possible for the dilution system to achieve equilibrium relatively quickly—ideally, in just a few seconds. Hence, the control system might be designed to achieve an optimal value for DF in a simple, sequential fashion. For example, one might start with some arbitrarily high dilution factor DF (e.g. using a relatively small value for $F_S$), guaranteed to yield a final particle concentration substantially lower than the coincidence limit of the sensor. Relatively little time would be needed to achieve equilibrium. Then, based on the achieved particle count rate, or concentration, the DF value could be decreased by an appropriate factor (through an increase in $F_S$, typically) to reach the desired final concentration. Additional changes in DF to "fine tune" the final concentration could be accomplished quickly, given the short residence time of the dilution chamber.

Alternatively, one can continue to adopt the method of fast estimation of the final equilibrium particle concentration $C_0/DF$ discussed above and in connection with the first embodiment of FIG. 5. That is, CPU/Controller 54 can be configured to measure automatically the initial rate of increase of C(t) vs t, called $R_{MAX}(0)$, as described by Equation 7. The value of $C_0/DF$ can then be quickly estimated from $R_{MAX}(0)$, as described by Equation 8, shortly after the start of the dilution process. This action permits the system to quickly change the value of dilution factor DF, typically by adjusting appropriately the flow rate $F_S$ of concentrated sample suspension by means of the control signal A6 generated by CPU/Controller 54.

The sample delivery means 56 can be any one of several means for capturing a quantity of concentrated sample suspension 22 from container 20, pulling it through tubing 24 and injecting it via tubing 10 into mixing chamber MC. These include: a variable-speed gear pump, variable-output peristaltic-type pump, programmable syringe pump (e.g. like pump SP used in the first embodiment of FIG. 5), variable-output fluid "metering" (including diaphragm-type) pump, or any other device which is able to deliver the concentrated sample fluid over an appropriate (possibly large) range of flow rates, adjustable by a suitable control signal A6 generated by CPU/Controller 54.

The diluted-sample delivery means 62 is shown as a peristaltic-type variable-output pump in FIG. 6A. However, as in the case of the concentrated sample delivery means, this delivery means can also be any one of several possible alternative devices, including those described above. The only requirement is that the output flow rate of the delivery means should be reasonably steady and adjustable to the desired value $F_2$ (typically, but not necessarily, fixed).

Figure 6B:
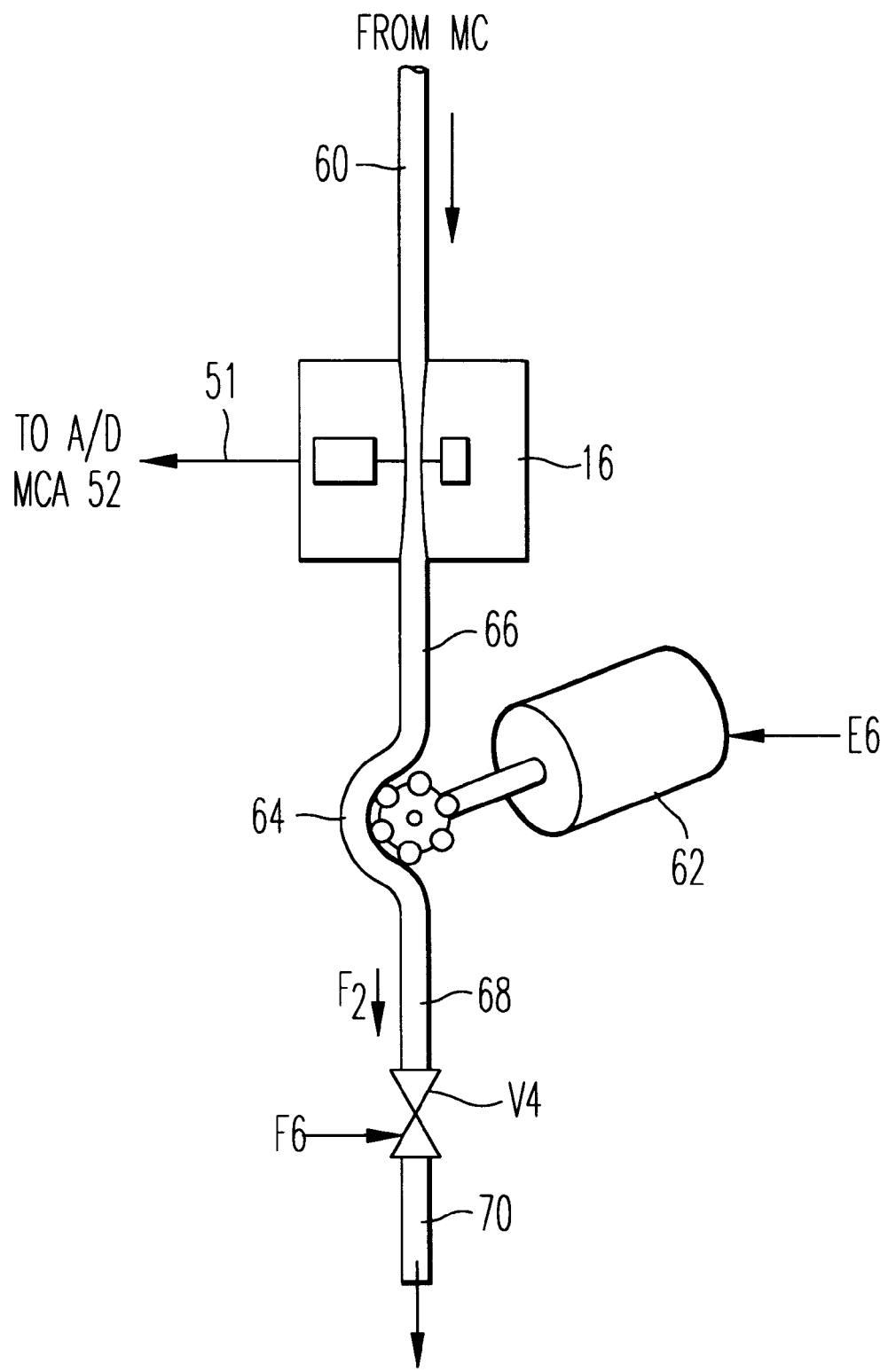
FIG. 6B is a diagram showing a portion of the embodiment of FIG. 6A with an alternative arrangement.

It should further be appreciated that pump/delivery means 62 can optionally be relocated to the drain side of SPOS sensor 16, as shown in FIG. 6B. As a consequence, the diluted sample suspension is pulled. rather than pushed, through sensor 16, thus reducing the possibility of contaminating or damaging the diluted sample suspension or otherwise altering its PSD before it passes through SPOS sensor 16 and is analyzed.

It should also be noted that drain valve V4 shown on the output side of sensor 16 in FIG. 6A, and also on the output side of delivery means 62 in FIG. 6B, is optional; whether it is required or even useful depends on the type of diluted-sample delivery means 62 which is utilized. Also, use of drain valve V3 which connects the main fluid flow output of mixing chamber MC to the drain is also optional.

It should be appreciated that there is a potentially significant disadvantage associated with the second embodiment of FIG. 6A. Larger amounts of diluent fluid and concentrated sample suspension will necessarily be consumed, compared to the needs of the first embodiment of FIG. 5, by a factor equal to that of the increase in their injection flow rates, for a given duration of dilution and PSA measurement, once the desired DF value is achieved. In the case of the sample suspension, this is typically unimportant, especially for high values of DF, for which only small amounts of sample suspension are used. On the other hand, relatively large amounts of fresh diluent fluid would be needed, which, depending on the fluid type and its cost, availability and disposal requirements, might pose a significant disadvantage.

Next, it is useful to consider the second approach suggested above for reducing the residence, or response, time t of the mixed-flow dilution process: namely, reduction of the fluid volume V of the mixing chamber. This approach forms the basis for the third embodiment of the invention, shown schematically in FIG. 7A.

In the third embodiment, the "mixing chamber" has evolved from a discrete, stirred container of significant fluid volume (typically $\geqq 10$ ml) to a "static" mixer SM of very small effective volume (typically 1–3 ml or less), requiring no stirring element. This well-known device consists of a convoluted network of stationary elements, arranged to interrupt the path of fluid flow in a tube or pipe in such a way as to disrupt the flow of individual arriving fluid streams, thereby inducing chaotic flow of the individual streams and ensuring that they become mixed together extensively before the fluid mixture exits the static mixer. The resulting diluted sample suspension which exits the static mixer should ideally be homogeneous—i.e. with a uniform particle concentration throughout the suspension. The residence time $\tau$ for the fluid mixing process is able to be reduced to a very short time—in practice, just 1–3 sec or less—without having to change the overall fluid flow rate F (equal to $F_D+F_S$) of the diluted sample suspension which flows through the sensor.

Fresh diluent fluid is delivered to static mixer SM of the dilution system by a delivery means/pump 30 in the same manner as described for the previous two embodiments. The diluent fluid flows through a main tube 84, which typically has a diameter similar to the diameter of static mixer SM. Concentrated sample suspension 22 is captured from container 20 through tubing 72 by sample delivery means 74/76, shown as a peristaltic-type pump including a motor drive 74 and pump head 76, including a curved section of tubing, in FIG. 7A. The sample suspension flows through tubing 77 and is injected into the main flow tube 84 upstream of static mixer SM, tubing 86, and sensor 16 by means of a suitable injection device 82—e.g. a fine tube, orifice or hollow needle. The dilution factor DF is adjusted as before, typically by varying the flow rate $F_S$ of concentrated sample suspension injected into the stream of diluent fluid flowing through tube 84 at a fixed flow rate $F_D$. The value of DF achieved after equilibrium is reached is determined by the ratio $F_D/F_S$, as in the previous embodiments. The injection flow rate $F_S$ of the concentrated sample suspension is adjusted by varying the output flow rate of the delivery pump 74/76, by means of an appropriate control signal A7 generated by CPU/Controller 54 and applied to the driving means (e.g. motor) 74 of the sample delivery pump 76.

Figure 7A:
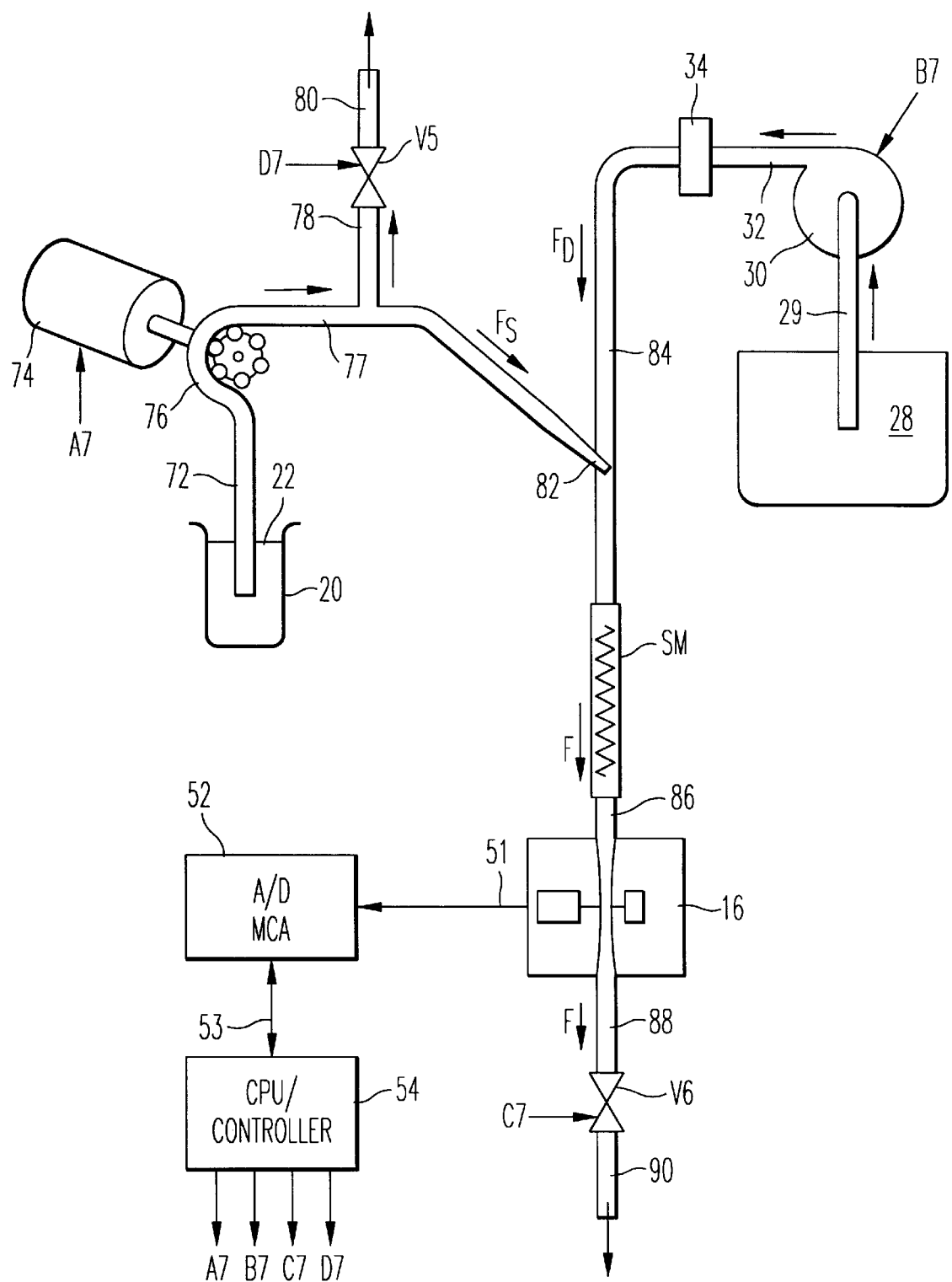
FIG. 7A is a diagram of a third embodiment of an automatic dilution system of the invention.

The remaining components in the system shown in FIG. 7A are substantially similar to those utilized in the first two embodiments. The drain valve V6, which is optional, is used to direct the diluted sample suspension stream exiting through tubing 88 from SPOS sensor 16 to a drain via tubing 90 and is actuated by control signal C7 generated by CPU/Controller 54. The sample bypass valve V5, actuated by control signal D7 generated by CPU/Controller 54, is used to divert unused concentrated sample suspension contained in tubing 72, 76 and 77 to a drain via tubing 78 and 80 or, optionally, back to sample source 22 after the dilution process and PSA measurement are completed. This function is useful when the system is flushed in preparation for capture and dilution of a new sample. As was the case for the first two embodiments, peristaltic-type pump 74/76 shown in FIG. 7A can be replaced by any of several other means which are deemed effective for delivering the concentrated sample suspension to the injector tube/orifice 82 (such as syringe pump SP seen in FIG. 5).

The overall operation of an automatic dilution system based on this third embodiment might appear to be substantially the same as that described in detail earlier for the first embodiment. However, there is an important quantitative difference in the behavior of this embodiment which obtains from the use of a static mixer SM of very small effective volume, compared to a conventional stirred mixing chamber of larger volume, as utilized in the first two embodiments. That difference is the speed of equilibration of the dilution process. The quantitative improvement in the settling, or response, time $\tau$ is responsible for a qualitative difference in the behavior of this third embodiment. As pointed out already, the effective "volume" V of the mixing "chamber" has now been greatly reduced relative to that which is obtained through the use of the more traditional dilution approaches adopted in the first and second embodiments. The actual size of the effective mixing volume utilized in this third embodiment may be difficult to determine in practice. However, all that effectively matters is its principal effect on the system: a significant, perhaps drastic, reduction in the residence time $\tau$ of the diluter. Hence, only a very short time—typically a few seconds or less—is needed for the particle concentration in the fluid stream exiting static mixer SM and entering SPOS sensor 16 to reach essential, steady-state equilibrium after the injection flow rate of either the sample or diluent fluid is changed by the control system. In effect, the final sample dilution factor, DF, can be adjusted almost instantaneously.

Because the response time can, in principle, be so significantly reduced through the effective use of such a small mixing volume, a different kind of control system can be designed and utilized, one which more closely resembles a conventional "negative feedback" scheme. A change in the injection flow rate $F_S$ of the concentrated sample suspension is translated nearly instantaneously into a new, stable value of the dilution factor DF. Hence, a final, optimal value for DF can be determined and implemented by the system almost immediately (i.e. after just a few seconds) after the starting sample suspension is first injected into the diluent flow stream.

In practice, this means that an "optimal" particle concentration can be achieved by an automatic dilution system based on this third embodiment using a variety of simple control "algorithms". For example, the system might be programmed to start diluting the starting sample suspension using a relatively large "trial" value for DF—i.e. a value designed to ensure that the final particle concentration lies well below any "optimal" concentration which may be dictated or established by the particular application of interest (or simply by the coincidence limit of the sensor). After just a few seconds following initial injection of the sample suspension into the flow system, final equilibrium of the dilution process will have been reached.

The control system can then easily determine by what factor the current, starting DF value should be decreased, in order to arrive at the larger, desired particle concentration. The sample injection flow rate $F_S$ can then be increased accordingly (i.e. by approximately the same factor as the desired decrease in DF). After a few additional seconds have elapsed, the dilution process will have arrived at equilibrium again, with a new, larger steady-state particle concentration (as determined from the particle concentration and sample injection flow rate $F_S$). If this concentration requires "fine tuning" to be closer to the desired value, the sample injection flow rate $F_S$ can be increased or decreased by an appropriate small factor. This change in $F_S$ is accomplished, of course, by transmitting the appropriate control signal A7 from CPU/Controller 54 to sample delivery means 74/76.

As time goes on during the dilution process, the particle concentration in the diluted sample suspension passing through the sensor can be periodically adjusted in the same fashion, to correct for changes in the particle concentration in the starting sample—e.g. due to time-dependent aggregation of "primary" particles, resulting from sample instability. In this case, the concentration of the largest particles in the sample will increase with time, likely requiring an increasing dilution factor DF over time. This capability provides a good example of the effective use of "negative feedback" to control the dilution process and is particularly useful for long-term "online" monitoring of the particle size distribution of suspensions and dispersions during sample production.

This fast, virtually real-time response of the dilution system to changes in the injection flow rate $F_S$ of the sample suspension now effectively obviates the need to determine the initial rate of change of the particle concentration $R_{MAX}(0)$ in order to estimate the final equilibrium concentration $C_0$/DF so as to make an "early" correction in the value of DF, as described earlier. Rather, the final particle concentration is now in principle attainable in a very short time, allowing the "optimal", desired concentration to be achieved quickly, simply by modifying the value of DF (through adjustment of $F_S$) appropriately.

As can be seen from the schematic diagram shown in FIG. 7A, there are fewer components required to implement this third embodiment than are needed for the first two realizations. However, it is useful to acknowledge that there are at least two potential disadvantages associated with the scheme shown in FIG. 7A. First, by its very design, a static mixer is susceptible to trapping or segregating larger, heavier particles, with resulting alteration of the underlying PSD in the suspension which emerges from the mixer, and also perhaps resulting in clogging of the mixer. Therefore, the approach advocated in the third embodiment is most effective when it is used with suspensions of relatively fine particles—ideally, those which are "colloidal" and relatively stable in suspension, having little tendency to settle out. Larger particles, which tend to settle easily in a slowly moving fluid stream, are often not compatible with static mixers, depending on the design of the static mixer and the fluid flow rates utilized.

Second, effective use of a static mixer for the purpose described herein presupposes that the flow rate of the fluid—in practice, the flow rate of the diluent fluid, when $F_D >> F_S$—is high enough to induce effective mixing within the mixing device. This will depend on the size and design of the static mixer. However, given a typical desired flow rate of 50–100 ml/min for many existing SPOS-type sensors, this assumption is often valid, especially for suspensions of very fine, colloidal particles. Otherwise, a significantly higher fluid flow rate may be needed to obtain effective mixing. One possible solution to this problem is to adopt the approach utilized in the second embodiment—i.e. increase both $F_D$ and $F_S$ substantially, so that the combined fluid flow rate F is high enough to achieve efficient mixing by the static mixer. Because this new flow rate is presumably too high for optimal performance of the SPOS sensor, one might split the output from the static mixer into two fluid streams of unequal flow rates (based on different tubing cross sections, for example). The higher-flow portion of the output stream would be directed to a drain, while the slower-flow portion of the diluted output stream would then be passed through the SPOS sensor for measurement.

Before proceeding to a description of the fourth embodiment, it is useful to consider a minor, but potentially useful, variation on the automatic dilution scheme just discussed. The motivation for this "modified" third embodiment is the realization that for some kinds of particle suspensions it may be desirable to avoid having the sample suspension come into direct contact with the sample delivery means—i.e. pump or other delivery device. This may be the case in order to avoid damaging (e.g. fracturing) the particles as they pass through the pump mechanism, or otherwise changing the underlying particle size distribution (e.g. promotion of aggregation). Alternatively, it may be desirable to prevent the concentrated sample suspension from coming into contact with the pump in order to avoid time-consuming and problematic cleanup of the latter, due to particles adhering to solid surfaces in the pump mechanism.

Figure 7B:
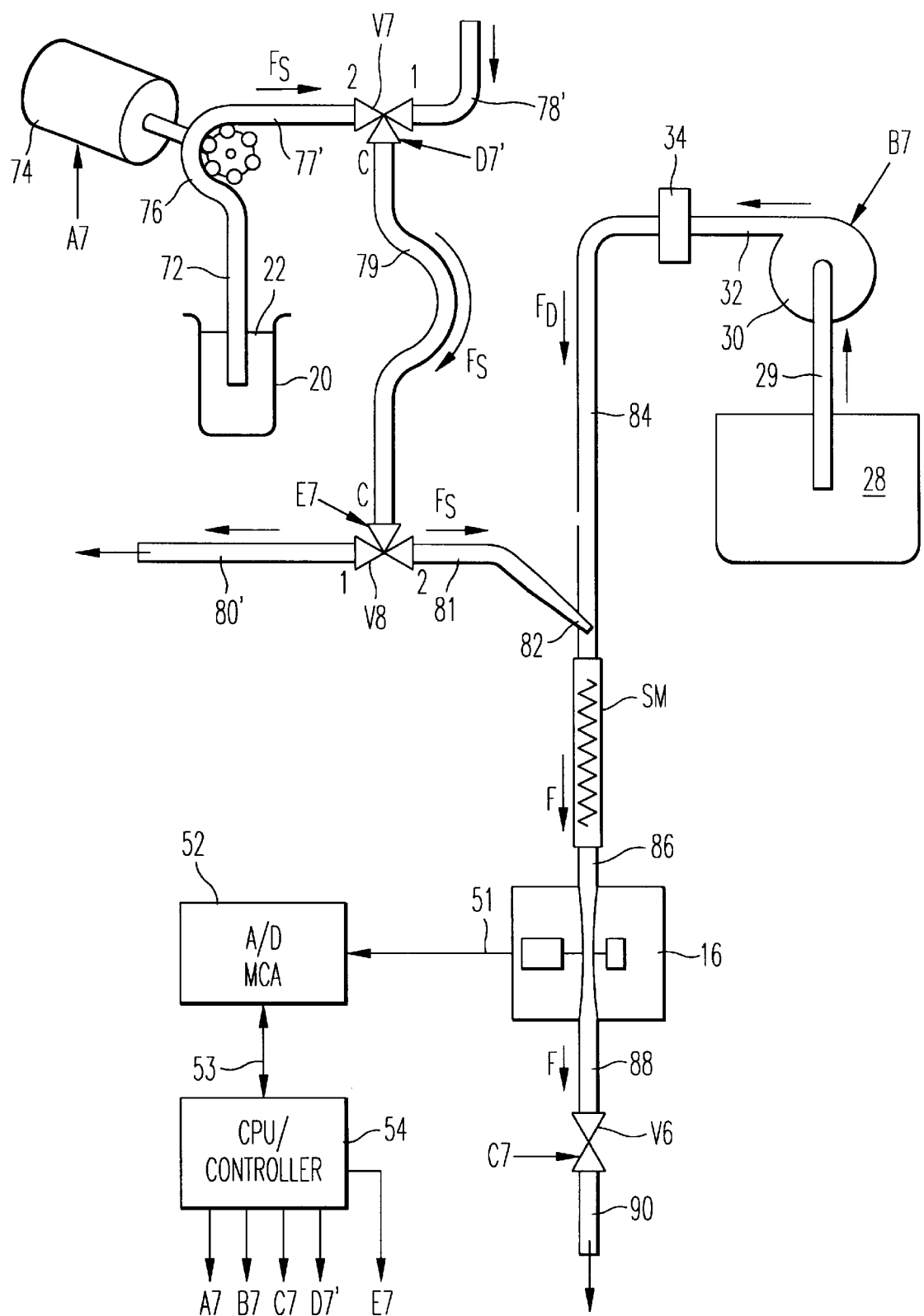
FIG. 7B is an alternative arrangement of the embodiment of FIG. 7A.

The modified system shown in FIG. 7B uses the same basic approach for diluting the concentrated sample suspension as adopted in FIG. 7A. As before, the sample suspension is injected at an adjustable flow rate $F_S$ into a stream of diluent fluid flowing at a (typically fixed) rate $F_D$. Static mixer SM efficiently mixes the two fluid streams, resulting in an approximately homogeneous stream of diluted sample suspension, with dilution factor $DF=1+F_D/F_S$ at equilibrium, which flows through SPOS sensor 16. However, the scheme shown in FIG. 7B differs from that shown in FIG. 7A in one respect: the captured portion of starting concentrated sample suspension is physically isolated from the mechanical delivery means which is used to deliver it to sample injector port 82.

An appropriate length of tubing 79, or some other suitable vessel of appropriate volume and shape, serves as a sample "capture reservoir", able to hold a quantity of concentrated sample suspension to be subsequently injected into the diluent fluid flow stream 84. Two 3-way valves, V7 and V8, actuated by control signals D7' and E7, respectively, generated by CPU/Controller 54, are used to accomplish this task. When valves V7 and V8 are switched to position "1", fluid can flow between ports "C" and "1" of each valve. Conversely, when V7 and V8 are switched to position "2", fluid can flow between ports "C" and "2" of each valve.

At the start of the dilution process, valves V7 and V8 are switched to position "1" by their respective control signals D7' and E7, generated by CPU/Controller 54, allowing concentrated sample suspension from an external source (not shown in FIG. 7B), assumed for the sake of this discussion to be under a small positive pressure, to flow through tubing 78', valve V7, "capture reservoir" (tubing) 79, valve V8 and finally tubing 80'. The sample suspension is then able to be discarded to a drain or to recirculate back to its original source. Under command of CPU/Controler 54, both valves V7 and V8 are switched to position "2", thereby closing off the capture reservoir 79 to the flow of fresh sample suspension. The sample suspension which is contained in the length of tubing 79 between the two valves is now available for injection by sample injector port 82 into tube 84 containing flowing diluent fluid.

An appropriate control signal A7 generated by CPU/Controller 54 is applied to delivery means 74/76, shown as a peristaltic-type pump in FIG. 7B, instructing it to pull diluent fluid 22 from container 20, through tubing 72, and to push it through tubing 77'. The fluid (plus possibly a quantity of residual air) being pumped through tubing 77' serves as a "hydraulic transmitter", able to push sample suspension contained in tubing 79 out of valve V8 and into tubing 81, without requiring the sample suspension and pump mechanism to come into contact with each other. After the residual sample suspension from the previous automatic dilution cycle residing in tubing 81 has been expelled from the latter through the injection tube/orifice 82 into the main diluent flow tube 84 (after a suitable time delay, depending on the volume contained in tubing 81), fresh concentrated sample suspension will reach the injection tube/orifice 82 and begin to be injected into the stream of diluent fluid flowing in tube 84.

At this point in the dilution process the system depicted in FIG. 7B will function in the same way as that described previously in FIG. 7A. After a suitable time (i.e. approx. $3\tau$, where $\tau$ is typically 2–3 sec or less for a static mixer of very small effective volume) has elapsed, the diluted sample suspension exiting static mixer SM and entering SPOS sensor 16 will have reached essentially constant concentration. This concentration can then be adjusted quickly by changing the dilution factor DF appropriately, by changing the flow rate of diluent fluid delivered "behind" the captured concentrated sample suspension in tube 79 by the controllable delivery means 74/76. The resulting flow rate $F_S$ of the concentrated sample suspension will necessarily be equal to the flow rate of the diluent fluid delivered by means 74/76. Given the typical relatively slow flow rate of the diluent fluid from means 74/76 and the design of the capture reservoir 79 (i.e. relatively long, thin tubing), there should be relatively little mixing of the diluent fluid supplied by delivery means 74/76 and the concentrated sample suspension contained in tubing 79. Movement of the sample suspension through tubing 79 should resemble "plug flow" conditions. In any case, the portion of sample suspension closest to the injection tube/orifice 82 should experience negligible dilution by the diluent fluid supplied by delivery means 74/76, assuming that the apparatus has been designed properly.

After the sample dilution and PSA measurement have been completed, valve V8 can be switched to position "1" again, by control signal E7. This action allows the diluent fluid delivered by means 74/76 to push sample suspension still remaining in the capture reservoir 79 through valve V8 and tubing 80 and out to a drain (or back to the original source). This action also serves to flush tubing 79 with diluent fluid, preparing it for the arrival of fresh concentrated sample suspension at the start of the next dilution/measurement cycle. The sample suspension remaining in tubing 81, between valve V8 and injection tube/orifice 82, will be injected into the diluent flow stream in tube 84 and ignored at the start of the next dilution cycle by waiting for a suitable length of time before data acquisition is allowed to begin, allowing fresh sample suspension to occupy the space in tubing 81 behind the previous sample.

Figure 8:
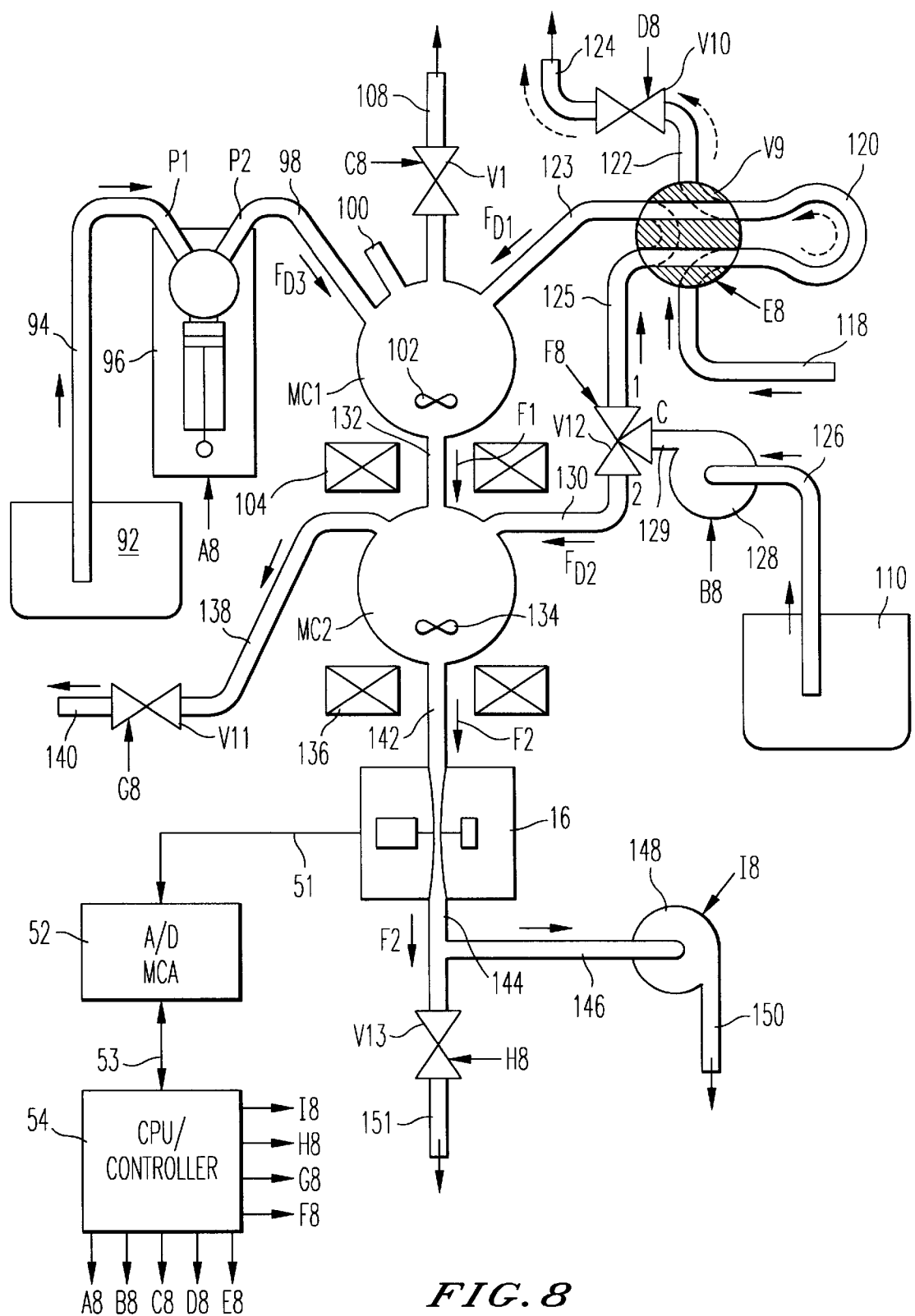
FIG. 8 is a diagram of a fourth embodiment of the invention.

A simplified schematic diagram of the fourth embodiment of the invention is shown in FIG. 8. Unlike the three previous embodiments, this scheme utilizes a two-stage dilution mechanism, with two mixing chambers and two sets of means for delivering diluent fluid and injecting sample suspension (original or prediluted). This more complicated method of diluting a starting concentrated sample provides two significant advantages over the previous embodiments.

First, it should be clear that this 2-stage scheme can achieve much larger values for the dilution factor DF than can otherwise be obtained, reliably and reproducibly, using just a single-stage dilution scheme. By using a first mixing chamber MC1 to supply prediluted sample suspension to a second mixing chamber MC2, the design shown in FIG. 8 can achieve DF values ranging from relatively small (i.e. 10–100 or lower) to very large (i. e. 10,000 or higher). The resulting increase in the dynamic range of the dilution factor is potentially very useful when applied to sample suspensions of widely varying composition, concentration and particle size distribution.

There is another potentially significant advantage associated with this 2-stage embodiment. The design shown in FIG. 8 facilitates the dilution of samples containing a significant population of large and/or dense particles which are prone to rapid settling in the suspended fluid. In general, such samples cannot be injected effectively into a mixing chamber at relatively low flow rates $F_S$ using the typical delivery means utilized in the previous three embodiments. However, such "difficult" samples can be handled relatively easily using the method adopted in this fourth embodiment of FIG. 8.

The first mixing chamber MC1 is used to perform a "first-stage", preliminary dilution of the starting concentrated sample suspension. The starting sample is conveniently introduced into mixing chamber MC1 using a "sample injection valve" V9, actuated either electrically or pneumatically by a control signal E8, generated by CPU/Controller 54. When valve V9 is in its "off" state (not energized) a sample "capture loop" 120 is connected in series with sample input tubing 118 and sample output tubing 122. As well, the diluent fluid input tubing 125 is connected to the output tubing 123. When valve V9 is switched to the "on" state (energized) by control signal E8, the sample capture loop 120 is placed in series with tubings 125 and 123 which is the condition shown in FIG. 8. This action allows the diluent fluid to push the sample suspension contained in the capture loop 120 out of valve V9 and into mixing chamber MC1 through tubing 123. Mixing chamber MC1 has an additional port 100 permitting the introduction of a sample suspension manually, if this should be desired.

As described above, the main function of valve V9 is to enable a fixed, predetermined volume of sample suspension to be "captured" from an external source and subsequently, upon command, to be "inserted" in series with the flow of diluent fluid which is allowed to enter predilution chamber MC1. However, it should be understood that this function can also be provided, as shown in FIG. 7B, by two 3-way valves V7 and V8 connected together by a length of tubing 79, which serves the function of capture loop 120. There are, however, two advantages to the use of a single, "6-way" valve, like V9, in FIG. 8, rather than two 3-way valves, like valve V7 and V8 in FIG. 7B. First, there is the obvious simplicity associated with the use of a single component, requiring only a single control signal. Second, and more importantly, there is the added ability conferred by the use of a 6-way injection valve like V9 to provide a "short circuit" through the valve in its "off" state. This allows diluent fluid to flow directly from tubing 125 to tubing 123, if desired, regardless of whether sample suspension has been allowed to fill capture loop 120.

Before the start of the dilution process, mixing chamber MC1 must be filled with fresh diluent fluid. The first "bleed" valve V1 is opened by means of a control signal C8, generated by CPU/Controller 54. In addition, a 3-way valve V12 is switched to position "1" (ports "C" and "1" connected) by control signal F8, also generated by CPU/Controller 54. Diluent delivery means/pump 128 is activated by control signal B8, generated by CPU/Controller 54, so that it pulls fresh diluent fluid from container 110 through tubing 126 and pushes it through valve V12 and tubing 125, through valve V9 and tubings 120 and 123 into mixing chamber MC1 at a desired flow rate $F_{D1}$. Diluent flow into mixing chamber MC1 is maintained long enough at the desired flow rate $F_{D1}$ so as to expel any residual air from mixing chamber MC1 through valve V1 and tubing 108 and permit thorough flushing of mixing chamber MC1, thus reducing the concentration of contaminant particles in MC1 to an acceptable, low level. Valve V1 is then closed by means of control signal C8, valve V12 is returned to position "2" by means of control signal F8 and the diluent delivery means/pump 128 is also turned off by means of control signal B8, thereby halting the flow of fresh diluent fluid into mixing chamber MC1.

Similarly, before the start of the dilution process, it is also generally necessary to flush, clean and fill the second mixing chamber MC2 with fresh diluent fluid. This is accomplished by opening the second "bleed" valve V11, by means of control signal G8, generated by CPU/Controller 54, leaving valve V12 in position "2" and energizing the diluent fluid delivery means/pump 128 at the desired flow rate $F_{D2}$, by means of control signal B8. Fresh diluent fluid is then pushed by the delivery means/pump 128 through valve V12 (ports "C" and "2") and tubing 130 and into mixing chamber MC2. Residual trapped air and excess diluent fluid flows out of mixing chamber MC2, through tubing 138, valve V11 and tubing 140 into a drain. Diluent fluid flow into mixing chamber MC2 is maintained long enough to ensure adequate flushing/cleaning of the chamber.

It should be noted that there is a simpler, alternative way in which mixing chamber MC2—indeed both mixing chambers MC1 and MC2—can be flushed, cleaned and filled with fresh diluent fluid prior to the start of the sample dilution process. Instead of opening valve V11, one can simply open valve V1, using control signal C8. Diluent fluid is then pumped by delivery means 128 through valve V12 and tubing 130 into mixing chamber MC2. Excess fluid will exit mixing chamber MC2, flowing upward (as seen in FIG. 8) into mixing chamber MC1. Excess fluid in mixing chamber MC1, in turn, will exit mixing chamber MC1, flowing through valve V1 and tubing 108 into a drain. Using this approach, both mixing chambers can be flushed, cleaned and filled with fresh diluent fluid at the same time, obviating the need for valve V11 and output tubing 138.

Before the start of the dilution process the sample capture loop 120, having volume $\Delta V_S$ (which can be preselected to the desired value using a piece of tubing of the appropriate size and length), must be filled with concentrated sample suspension. Valve V10 is opened, actuated by control signal D8, generated by CPU/Controller 54. This action allows concentrated sample suspension, obtained from an external source not shown in FIG. 8 and assumed to be under positive pressure, to flow through input tubing 118 into valve V9, through the sample capture loop 120, back out of valve V9, through output tubing 122 and valve V10 and then out through tubing 124 to a drain (or, optionally, back to the original sample source or other container). Valve V10 is then closed, actuated by control signal D8, in order to "capture" concentrated sample suspension in tubing 120.

The sample dilution process can now commence. First "bleed" valve V1 is opened by means of control signal C8, and valve V12 is switched to position "1" by control signal F8. Fresh diluent fluid is pulled from container 110 through tubing 126 by the diluent delivery pump 128, with the output flow rate $F_{D1}$ adjusted to the desired value by control signal B8. The diluent fluid passes through valve V12 and input tubing 125 into valve V9 and through sample capture loop 120, pushing the captured sample suspension ahead of it, back out of valve V9, through output tubing 123 and into the first mixing chamber MC1. This action serves to deliver the quantity of sample suspension contained in capture loop 120 into mixing chamber MC1. Valve V12 is then switched back to position "2" by control signal F8. The diluent fluid must be made to flow for a length of time just sufficient to push the entire volume $\Delta V_S$ of sample suspension into mixing chamber MC1, and not longer. In this way, the volume $\Delta V_S$ of sample will displace an equal volume of diluent fluid initially residing in mixing chamber MC1 (causing it to exit through valve V1), and no more. The prediluted sample suspension in mixing chamber MC1 is mixed using an electromagnetic stirrer comprising winding 104 and associated circuit means and magnetic stir bar 102, as shown in FIG. 8, or instead by a mechanical stirring mechanism.

At this point in time, mixing chamber MC1 contains prediluted sample suspension, where the "first" dilution factor DF1 is given approximately by the quantity $V_1/\Delta V_S$, where $V_1$ is the volume of fluid contained in mixing chamber MC1. ($V_1$ will be smaller than the physical internal volume of mixing chamber MC1 if the latter is only partially filled with diluent fluid at the time of sample injection.) The word "approximately" is used above to convey the fact that DF1 will not be precisely equal to the theoretical value above, because a small fraction of the injected sample suspension will typically be lost to the drain through valve V1 if mixing chamber MC1 was initially filled with fresh diluent fluid at the time of sample injection. The prediluted sample suspension residing in mixing chamber MC1 is then used as a source of "sample" for the second stage of the dilution process, provided by mixing chamber MC2 and the associated means for sample/diluent injection/delivery. The second stage of the dilution system closely resembles the single-stage dilution system of the first embodiment, shown in FIG. 5.

A variable-output fluid delivery device, shown as a programmable syringe pump 96 in FIG. 8 (similar to syringe pump SP shown in FIG. 5 in connection with the first embodiment), is instructed by control signal A8, generated by CPU/Controller 54, to capture a quantity of diluent fluid 92 through tubing 94 and input port P1 and fill the syringe. Control signal A8 then directs syringe pump 96 to expel the diluent fluid through output port P2 and tubing 98 at a controlled (and adjustable) flow rate $F_{D3}$ into mixing chamber MC1. Owing to the incompressibility of the diluent fluid, this action causes the prediluted sample suspension (with dilution factor DF1) residing in mixing chamber MC1 to exit through output tubing 132 and enter mixing chamber MC2 at the same flow rate $F_{D3}$ (shown as F1 in FIG. 8, where F1=$F_{D3}$) It is assumed that at this stage of the dilution process, valve V13 has been opened by control signal H8, generated by CPU/Controller 54.

Fresh diluent fluid entering mixing chamber MC1 on a continuous basis during the dilution process causes the particle concentration in the fluid exiting mixing chamber MC1 and entering mixing chamber MC2 to become further diluted over time. The concentration decays exponentially with time, where the decay time constant $\tau$ equals $V_1/F_{D3}$. However, flow rate $F_{D3}$ is typically so low, volume $V_1$ of chamber MC1 so relatively large, and the total dilution/ measurement time so relatively short, that this additional extent of dilution of the sample suspension exiting mixing chamber MC1 and entering mixing chamber MC2 over time can often be ignored.

Valve V12 remains in position "2", connecting ports "C" and "2". Fresh diluent fluid 110 is pulled through tubing 126 and pushed through tubing 129, valve V12 and tubing 130 by diluent delivery means 128, with output flow rate $F_{D2}$ adjusted by control signal B8, generated by CPU/Controller 54. The diluent fluid flows continuously into mixing chamber MC2, with the fluid/particle contents stirred continuously by an electromagnetic stirrer comprising winding 136 and associated circuit means and magnetic stir bar 134, as shown in FIG. 8 or, alternatively, a suitable mechanical stirring mechanism.

After equilibrium in the mixing process is reached in mixing chamber MC2 (as described earlier, where the response, or residence, time $\tau$ equals $V_2/F_2$, where $V_2$ is the fluid volume in mixing chamber MC2 and F2=$F_{D2}$+$F_{D3}$), the sample suspension which exits mixing chamber MC2 and passes through SPOS sensor 16, at flow rate F2=$F_{D2}$+$F_{D3}$, will be further diluted relative to the prediluted sample suspension residing in mixing chamber MC1. The "second" dilution factor DF2 is given by the ratio of the total flow rate, $F_{D2}$+$F_{D3}$, to the prediluted sample flow rate $F_{D3}$. The overall dilution factor DF achieved by this 2-stage automatic dilution system is therefore approximately given by $$DF=DF1 \times DF2 \approx (V_1/\Delta V_S)(1+F_{D2}/F_{D3}) \quad (9)$$

As was the case earlier for the other embodiments, the second-stage diluent fluid flow rate $F_{D2}$ is normally held constant at a value which is recommended for optimal performance of the SPOS sensor (typically in the range of 25–200 ml/min). Therefore, the extent of overall dilution DF of the starting sample suspension by the 2-stage apparatus is typically adjusted by varying the flow rate of injection $F_{D3}$ of diluent fluid into mixing chamber MC1, by means of the variable-output diluent delivery means 96, such as a programmable syringe pump SP device. It is this rate which would be controlled automatically, using control signal A8 generated by CPU/Controller 54, in order to achieve an "optimal" particle concentration in the diluted sample suspension which passes through the SPOS sensor, as defined and discussed previously.

It is presumed that the dilution factor DF1 achieved in the first stage of the apparatus is not larger than the final factor DF which is ultimately desired, because DF1 effectively sets a lower limit on the value for the overall factor DF. Typically, it is convenient to utilize a value for DF1 in the range of 10–100. For example, if volume $V_1$ of mixing chamber MC1 equals 50 ml, then $\Delta V_S$ would vary between 5 ml (DF1=10) and 0.5 ml (DF1=100). Depending on the available range for $F_{D3}$ provided by the diluent fluid deliver means 96, the value for DF can be adjusted accordingly. For example, one can assume a second-stage diluent fluid flow rate $F_{D2}$ equal to 60 ml/min, or 1 ml/sec, and a first-stage diluent fluid injection flow rate $F_{D3}$ which ranges from 0.1 ml to 0.001 ml/sec. With DF1=10, the final dilution factor DF will range from 110 to 10,010. In the case of DF1=100, DF will vary from 1,100 to 100,100.

Next, it is useful to consider a modification of the two-stage automatic dilution process described above. The use of a first predilution stage before implementation of automatic mixed-flow dilution has the major advantage of accommodating samples of widely varying concentration and particle size distribution. The only potentially significant disadvantage of the scheme adopted for the fourth embodiment is the length of time needed for the second stage to reach equilibrium, given the typical relatively large volume $V_2$ of the second mixing chamber MC2. Hence, it is useful to consider replacing the conventional stirred mixing chamber MC2 of FIG. 8 with the static mixer SM utilized in the third embodiment and its variation, shown in FIGS. 7A and 7B, respectively.

Figure 9:
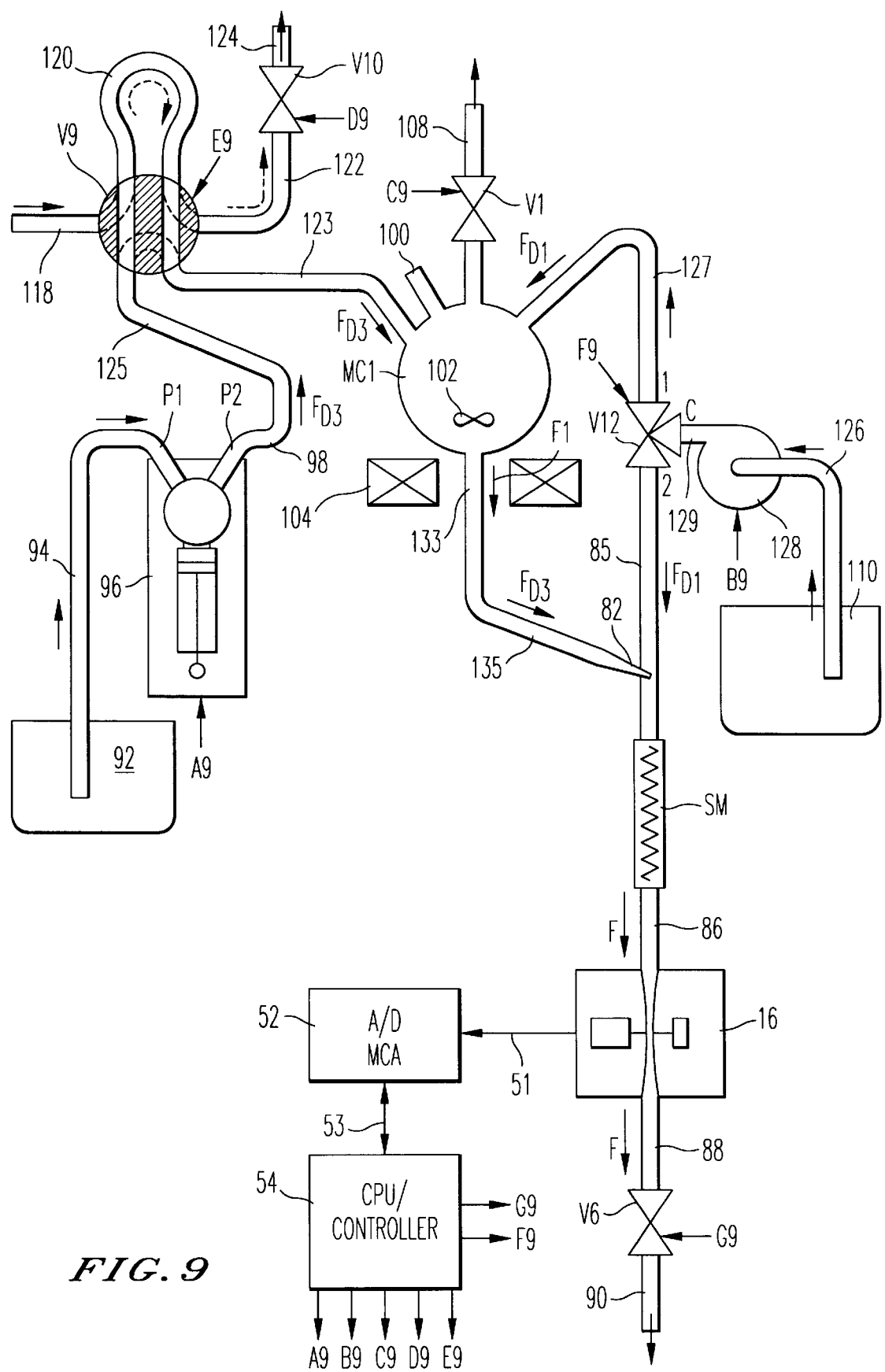
FIG. 9 is a diagram of a fifth, and preferred embodiment, of an automatic dilution system of the invention.

Combining the most useful features of the third and fourth embodiments forms the basis for the fifth, and preferred embodiment, shown schematically in FIG. 9. The design of the fluidics system for the first predilution stage in the fifth embodiment of FIG. 9 has been modified relative to the design employed in the fourth embodiment of FIG. 8. In FIG. 9 sample capture valve V9 is now located between prediluted sample "transmission" means 96 and predilution chamber MC1, rather than between diluent delivery means 128 (and valve V12) and predilution chamber MC1, as shown in FIG. 8. This change in fluidics design is potentially advantageous in at least two respects, as discussed below.

From the embodiment of FIG. 8, the fifth embodiment of FIG. 9 incorporates first mixing chamber MC1, an electromagnetic stirrer comprising winding 104 with associated circuit means and magnetic stir bar 102, concentrated sample capture loop 120, sample suspension supply pipe 118, diluent supplies 110 and 92 (optionally one and the same), diluent delivery means 96 and 128, valves V1, V9, V10 and V12 and associated tubings, similar (but not identical in all respects) to the tubings as described in the above description of the embodiment of FIG. 8. From the embodiment of FIG. 7A, the embodiment of FIG. 9 incorporates a flow tube 85 corresponding to flow tube 84 of FIG. 7A, static mixer SM, tubing 86, SPOS sensor 16, tubing 88, valve V6 and tubing 90, leading to a drain. In FIG. 9, prediluted sample suspension is fed from predilution chamber MC1 through tubing 133 corresponding to tubing 77 of FIG. 7A, and injection nozzle 82 into tubing 85 upstream from SPOS sensor 16. As in all prior embodiments, SPOS sensor 16 provides the detected signal waveform on line 51 to AD/MCA 52 (analog-to-digital converter and multichannel analyzer), which communicates with CPU/Controller 54, which generates control signals A9–G9. Having described the operation of these components and subsystems in adequate detail in connection with the above descriptions of the embodiments of FIGS. 7A and 8, it is not necessary to provide a complete description of the operation of the embodiment of FIG. 9. However, because the arrangement of key components in FIG. 9 have been changed relative to FIG. 8, it is necessary to summarize the operation of the preferred system of FIG. 9.

As before, automatic sample injection valve V9 actuated by control signal E9, generated by CPU/Controller 54, is used to capture a quantity of concentrated sample suspension of predetermined volume $\Delta V_S$ in sample capture loop 120 from an external source via tubing 118. The fluidic path taken by the sample suspension during the filling of capture loop 120, when valve V9 is in its "off" state and valve V10 is switched open, has already been described. However, there is a significant difference in the design and operation of the first predilution stage of the system shown in FIG. 9, compared to the design and operation of the scheme utilized in the fourth embodiment of FIG. 8, which requires description.

In FIG. 9, sample "transmission" means 96 is used to inject diluent fluid into predilution chamber MC1 for the purpose of causing prediluted sample suspension to exit chamber MC1 at a controllable flow rate $F_{D3}$ and become mixed in static mixer SM with diluent fluid flowing at a rate $F_{D1}$ in order to achieve a second dilution of the sample suspension, as described in connection with the fourth embodiment of FIG. 8. However, unlike the system in FIG. 8, the system shown in FIG. 9 places valve V9, and therefore sample capture loop 120, in the fluid path between sample "transmission" means 96 and predilution chamber MC1.

As a result of this design change, sample "transmission" means 96, rather than diluent fluid means/pump 128, is utilized to push volume $\Delta V_S$ of concentrated sample suspension out of capture loop 120 and into predilution chamber MC1. This modification in fluidics design utilized in the fifth embodiment of FIG. 9 results in an improvement in the overall performance of the automatic dilution system. First, and most significantly, this new scheme permits the captured volume $\Delta V_S$ of concentrated sample suspension to be injected with greater accuracy and reproducibility into predilution chamber MC1, because of the use of a more accurate and controllable delivery means, like the programmable syringe pump SP utilized in both FIG. 8 and 9, than would be the case using a more conventional delivery pump, like diluent fluid delivery means 128, which is utilized in both FIGS. 8 and 9 to deliver diluent fluid continuously into tube 85 for the purpose of mixing with prediluted sample suspension in an appropriate mixing vessel (i.e. stirred mixing chamber MC2 in FIG. 8 and static mixer SM in FIG. 9). A syringe pump SP can in general control more precisely the flow of diluent fluid passing through valve V9 and sample capture loop 120, so that the entire volume $\Delta V_S$ of captured sample suspension can be made to enter predilution chamber MC1, with negligible "undershoot" and also negligible "overshoot", resulting in inadvertent injection of a quantity of diluent fluid into predilution chamber MC1.

There is a second advantage associated with the modified fluidics design used for the predilution stage in the fifth embodiment of FIG. 9. After the sample capture and predilution processes have been completed, the second-stage continuous dilution process is initiated, requiring continuous injection of fresh diluent into predilution chamber MC1 at a controllable flow rate $F_{D3}$, as described in connection with the fourth embodiment of FIG. 8. With the new scheme of FIG. 9, the diluent fluid is delivered by the same device, delivery means 96, which was just used to "transmit" concentrated sample suspension into predilution chamber MC1, as described above. Hence, diluent fluid is caused to flow on a continuous basis through valve V9, sample capture loop 120, and tubings 125 and 123 on route to predilution chamber MC1. This action serves the useful purpose of flushing out into predilution chamber MC1 any residual (presumably small) amounts of concentrated sample suspension which may have been left behind (i.e. adhering to surfaces) in the above mentioned fluidic path during the initial predilution process.

Before the captured sample is injected into predilution chamber MC1, chamber MC1 is flushed and filled with fresh diluent fluid, as described for the fourth embodiment of FIG. 8. Fresh diluent fluid, supplied by delivery means 128, which is controlled by signal B9, generated by CPU/Controller 54, is pumped through valve V12 (in state "1") and proceeds directly into predilution chamber MC1 via tubing 127. Excess fluid exits chamber MC1 via valve V1 (switched open by control signal C9) and tubing 108 to a drain. After sufficient time has elapsed to ensure adequate flushing/cleaning of predilution chamber MC1 with diluent fluid, the remaining parts of the fluidics system can optionally be flushed and cleaned, thereby reducing the concentration of background contaminant particles to a tolerably low level.

The flow path for prediluted sample suspension, consisting of predilution chamber exit port 133, tubing 135 and injector/orifice 82, are flushed by closing valve V1, by means of control signal C9, and opening sensor drain valve V6, by means of control signal G9, generated by CPU/Controller 54. Fresh diluent is thus allowed to flow into predilution chamber MC1, as described above in connection with the flushing/cleaning of chamber MC1, and then out of chamber MC1, through tubings 133 and 135 and injector/orifice 82, into main flow tube 85, through static mixer SM and sensor 16 and out to a drain via tubing 88, valve V6 and tubing 90. The remainder of the fluidics system, consisting of main flow tube 85 connecting injector/orifice 82 and valve V12, can be flushed with fresh diluent fluid by switching valve V12 to state "2", by means of control signal F9, thereby allowing diluent fluid supplied by delivery means 128 to flow through tube 85, static mixer SM, sensor 16, tubing 88, valve V6 and tubing 90 to a drain.

During these flushing/cleaning operations the flow rate of diluent fluid $F_{D1}$, determined by signal B9 controlling delivery means 128, is typically increased significantly above the "normal" rate appropriate for the sensor and used to carry out a PSA measurement, in order to shorten the time needed to complete these operations. At the same time, the particle concentration remaining in the fluidics system can be determined by monitoring the particle count rate (in the entire measurable size range or, alternatively, over a portion thereof, as desired) and converting this information to an equivalent concentration using the known diluent flow rate $F_{D1}$. (It is usually desirable to decrease $F_{D1}$ to its "normal" value appropriate for the sensor during the subsequent PSA measurement.)

After the system has been adequately flushed/cleaned, automatic sample dilution can commence. Volume $\Delta V_S$ of concentrated sample suspension, previously captured by loop 120 attached to valve V9, is introduced into predilution chamber MC1 using diluent fluid, supplied by sample "transmission" means 96. After this step is completed, chamber MC1 will contain prediluted sample suspension, with dilution factor $DF1 \approx V_1/\Delta V_S$. This prediluted sample suspension is then ready for injection (via exit port 133, tubing 135 and injector/orifice 82) into flow tube 85, carrying diluent fluid at flow rate $F_{D1}$ supplied by delivery means 128 (through valve V12, switched to state "2" by control signal F9). As described in connection with the fourth embodiment of FIG. 8, sample "transmission" means 96 is used to deliver fresh diluent fluid 92 into chamber MC1 (via tubings 94, 98, 125 and 123) at an adjustable flow rate $F_{D3}$ in order to cause an equal quantity of prediluted sample suspension to exit predilution chamber MC1 and be injected (after filling exit port 133, tubing 135 and injector/orifice 82) at the same flow rate into the diluent fluid stream in tube 85 and then into static mixer SM. The two fluids are combined in the static mixing means SM, ideally yielding a homogeneous particle concentration in the fluid exiting static mixer SM and flowing through sensor 16 at the flow rate $F=F_{D1}+F_{D3}$.

After the mixing process in static mixer SM reaches essential equilibrium—i.e. after an elapsed time of approximately $3\tau$, where $\tau$ is the "settling", or residence, time of static mixer SM (typically just a few seconds, or less)—the extent of additional dilution yielded by the second-stage process is given by $DF2=F/F_{D3}=1+F_{D1}/F_{D3}$. The essential difference in the behavior of this dilution system, compared to the behavior of the system shown in FIG. 8, is that in principle the response time $\tau$ for the second dilution stage can be made much shorter through the use of a static mixer SM of much smaller effective volume than the volume of the stirred mixing chamber MC2 in FIG. 8. In addition, the apparatus is simplified, eliminating the need for additional stirring components and related parts.

Depending on the nature of the starting sample suspension and the criteria established for predetermining an "optimal" particle concentration, the automatic control system increases or decreases the second-stage dilution factor DF2 by decreasing or increasing, respectively, the flow rate $F_{D3}$ of diluent fluid delivered to predilution chamber MC1 by sample transmission means 96, using an appropriate control signal A9 as described previously in connection with the fourth embodiment of FIG. 8. After sufficient time (i.e. $2\tau$–$3\tau$) has elapsed to allow the particle concentration to reach essential equilibrium, the PSD can be obtained in the usual way, using a desired starting threshold for particle diameter. When sufficient data have been collected to yield results of acceptable statistical accuracy, transmission means 96 is instructed by control signal A9 to stop delivering diluent fluid to predilution chamber MC1. The entire fluidics system can then be flushed in the manner outlined above.

Figure 10:
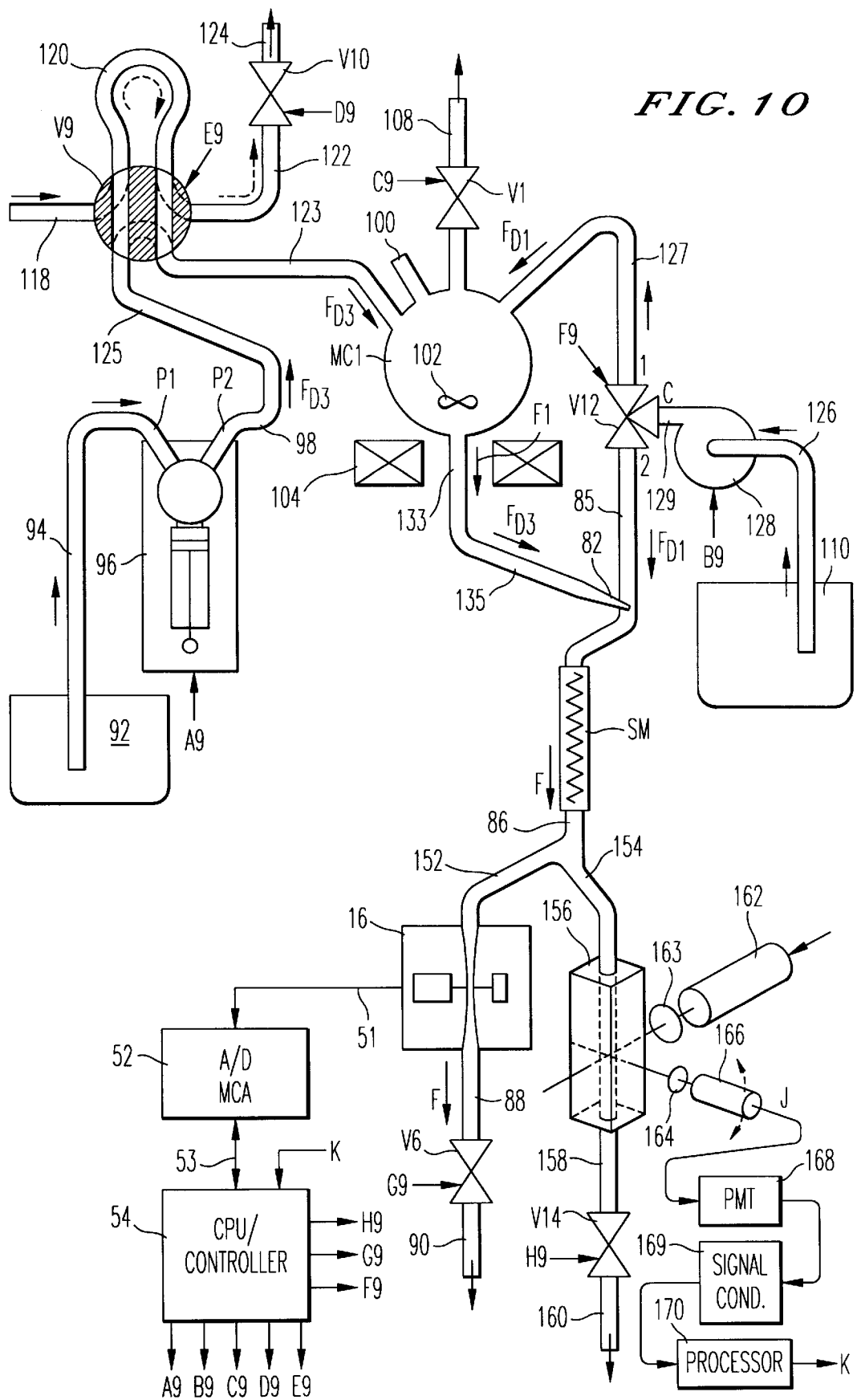
FIG. 10 is a diagram of a variant of the embodiment of FIG. 9.

A variant of the fifth embodiment of this invention is shown schematically in FIG. 10. The various means used to dilute the starting concentrated sample are identical to those seen in FIG. 9 and described above. A sample capture valve V9, actuated by control signal E9, is used to capture a known volume of concentrated sample suspension $\Delta V_S$ in the sample capture loop 120. This quantity of sample is then injected into volume $V_1$ of fresh diluent contained in predilution chamber MC1, thereby reducing the particle concentration of the original sample suspension by a predilution factor DF1 approximately, where DF1 equals $V_1/\Delta V_S$, as was the case for the fifth embodiment of FIG. 9.

The sample "transmission" means 96, shown in FIG. 10 as a variable-output, programmable syringe pump, is instructed by control signal A9 to deliver fresh diluent fluid from source 92 into chamber MC1 at a controlled flow rate $F_{D3}$. This action causes the prediluted sample suspension residing in chamber MC1 to exit through tubings 133 and 135 at the same flow rate $F_{D3}$ and to be injected via injection nozzle/orifice 82 into the main flow tube 85. Meanwhile, fresh diluent is caused to flow through tube 85 by delivery means 128 at a flow rate $F_{D1}$ controlled by signal B9, which is generally (but not necessarily) constant. The diluent fluid and prediluted sample suspension become comingled and randomly mixed in static mixer SM, so that the fluid exiting mixer SM, at the flow rate $F_{D1}+F_{D3}$, is ideally homogeneous with respect to particle concentration. The extent of additional dilution of the prediluted sample suspension contained in chamber MC1 achieved by the mixed-fluid process is given by $DF2=(F_{D1}+F_{D3})/F_{D3}=1+F_{D1}/F_{D3}$, as described above for the fifth embodiment of FIG. 9.

As was also explained earlier, the continuous addition (albeit at a relatively low flow rate) of a small amount of diluent fluid to predilution chamber MC1 by delivery means 96 causes the prediluted sample suspension contained in chamber MC1 to be additionally diluted to a small, increasing extent continuously over time. This additional dilution has an exponential time dependence, with the particle concentration in the fluid exiting chamber MC1 decreasing in time according to the exponential factor $\exp(-V_1/F_{D3})$, as described earlier and in greater detail by Nicoli et al in U.S. Pat. No. 4,794,806. As pointed out above, the effect of this continuous (albeit usually small) extent of dilution of the prediluted sample suspension exiting chamber MC1 can be computed relatively accurately using the exponential function above, so that its effect on the amount of original sample material which exits static mixer SM and flows through SPOS sensor 16 per unit length of time can be determined quantitatively. Such a calculation permits a more accurate "mass (volume) balance" to be performed on a sample. That is, following an SPOS-type measurement of the PSD for particle diameters $d \geq d_o$, one can determine the fraction of the total volume of all particles passing through the SPOS sensor represented by any given portion of the measured PSD.

The scheme shown in FIG. 10 differs from that seen in FIG. 9 in only one, significant respect. The flow of doubly-diluted sample suspension exiting static mixer SM is now able to flow through an additional device which is sensitive to the suspended particles, rather than through only SPOS-type sensor 16, as previously described. The diluted suspension which exits static mixer SM through tube 86 is allowed to flow through either branch tube 152 and SPOS sensor 16 in the "normal" fashion described above for all five embodiments of the invention, or, alternatively, branch tube 154 and an appropriate light scattering cell 156, used to carry out an alternative kind of PSD measurement of the sample suspension, using a technique completely different from the SPOS method. The output fluid from device SM can be made to flow through SPOS sensor 16 and tube 88 by opening valve V6 (typically to a drain, via tubing 90) and closing valve V14, by means of control signals G9 and H9, respectively, generated by CPU/Controller 54. Alternatively, the fluid exiting device SM can be made to flow through scattering cell 156 and tube 158 by closing valve V6 and opening valve V14 (typically to a drain, via tubing 160), again by means of the same respective control signals.

The additional, alternative PSA measurement technique depicted in FIG. 10 is that of dynamic light scattering (DLS), also known as photon correlation spectroscopy (PCS). A laser diode 162 or other coherent light source is used to provide a collimated light beam, which is focused by lens 163 into the center of scattering cell 156. A portion of the light which is scattered by the suspended particles in the cell is captured by an optical element 164 (e.g. a pinhole of appropriate size and distance from the scattered light source) and an optical fiber 166 and thereby transmitted as scattered light signal J to a suitable detector—e.g. photomultiplier tube, or "PMT" 168. The fluctuations in the resulting PMT detector photocurrent caused by random Brownian motion, or diffusion, of the suspended particles is processed electronically, after suitable signal conditioning by signal conditioning means 169 (a preamplifier and d.c. level discriminator circuit), typically using a digital autocorrelator in processor 170 in which the resulting autocorrelation function is "inverted" by an appropriate mathematical algorithm, in order to obtain a representation K of the overall intensity-weighted PSD for all of the suspended particles. (A more physically meaningful volume-weighted PSD is obtained from the intensity-weighted PSD using the relationship between the scattered intensity and the diameter of a (spherical) particle, provided by classical (Mie) light scattering theory). The representation K is fed as an input to CPU/Controller 54 and also, optionally, to an external computer.

The PSD obtained using the DLS technique provides a broad-brush "overview" of the size distribution of all of the particles in the sample suspension. The well-known DLS technique is useful for characterizing the PSD for "mostly-submicron" samples, for which the great majority of particles are smaller than one micron. The SPOS technique is then used to provide a complementary, detailed "close-up" picture of the large-diameter "tail" of the PSD, typically above 0.5 or 1.0 $\mu$m. As described above in connection with FIGS. 4A and B, the total particle volume fraction contained in this outlier "tail" portion of the PSD often correlates strongly with the occurrence of defective behavior of the sample, in terms of stability or final physical or chemical properties. This is often the case, notwithstanding the fact that the tail portion of the PSD may represent only a very small fraction of the total particulate volume, or mass, in the sample. The purpose of the modified fifth embodiment of FIG. 10 is to permit a PSA measurement to be made using the automatic dilution system described herein which also includes an "overview" of the entire PSD for a mostly-submicron sample, which is responsive to all of the particles, including the majority, which lie outside the range of sensitivity of the SPOS sensor utilized in the system (i.e. smaller than the minimum detectable/measurable particle size for the SPOS sensor).

As is well known, the DLS method is an "ensemble" technique, in which a large number of particles contribute simultaneously to the "signal" generated—i.e. the scattered light intensity at a given scattering angle (chosen as an example to be 90° in FIG. 10). The resulting PSD is obtained by mathematical manipulation of a quantity derived from the scattered light intensity, the intensity autocorrelation function. This situation is in sharp contrast with the SPOS method, in which the sample must usually be diluted even further, to a sufficient extent that the "signal" (a single pulse in voltage) is representative of a single particle, as it passes through the active sensing zone of the sensor. Hence, the manner in which the automatic dilution system, described earlier, is used in conjunction with the alternative DLS subsystem shown in FIG. 10 will be different from the operation described earlier for the SPOS sensor alone. It is useful to describe a typical sequence of operations for a dual-stage automatic dilution system which is designed to "feed" both an SPOS sensor and a DLS optical system, as shown in FIG. 10, in serial fashion. It should be noted and appreciated that the combined SPOS-DLS scheme shown in FIG. 10 and discussed below can also be utilized in conjunction with the automatic dilution systems shown in the other four embodiments.

The DLS technique generally requires that the diluted sample suspension be stationary—not flowing. The resulting temporal fluctuations in the scattered light intensity which are captured by the optical system, processed electronically and analyzed mathematically therefore properly result from the random Brownian motion of the suspended particles due to diffusion. The scattered light signal must be collected, processed and analyzed for an extended period of time, typically 3–5 minutes or longer, where the time needed depends on the level of statistical accuracy required in the autocorrelation function so as to produce computed PSD results of acceptable accuracy and stability. It is therefore convenient to begin the automatic dilution process for the combined SPOS-DLS system by first establishing an appropriate dilution factor for the DLS subsystem, so that it can begin to accumulate and process data, prior to establishing another, usually different, dilution factor for the SPOS subsystem.

Hence, it is usually preferable to start the measurement sequence by keeping valve V6 closed and opening valve V14, by means of the control signals G9 and H9, respectively. The diluted sample suspension which exits the SM device is thus caused to flow through scattering cell 156, rather than through SPOS sensor 16. The automatic dilution process is then initiated in a manner similar to that described earlier for the fifth embodiment of FIG. 9. There is an important difference, of course. In the present case, the average intensity of the scattered light signal J captured by optical element 164 and optical fiber 166 produced by an ensemble of suspended particles in scattering cell 156 is used by means of signal K to inform the automatic dilution system whether the value of the second dilution factor DF2 is correct—rather than using the particle count rate, or equivalent particle concentration over some size range, obtained from the SPOS sensor 16, as described for all of the previous embodiments.

Prior to initiating the sequential automatic dilution process, the operator must stipulate, by means of an input into a suitable control menu in the operating software of CPU/Controller 54, or by means of an appropriate switch, potentiometer or other hardware input device, the desired level of the average scattered light intensity which is to be achieved for optimal operation of the DLS subsystem, in order to achieve the most reliable and accurate PSD results in the shortest period of time. On the one hand, too low a level of average scattered intensity will result in an unacceptably high level of statistical noise in the autocorrelation function, as well as excessive sensitivity to impurities in the suspending fluid and other noise sources in the DLS subsystem. On the other hand, too high a level of scattering intensity invites distortion of the autocorrelation function and the resulting computed PSD due to the effects of interparticle interactions and/or multiple scattering. Typically, one would choose a level of average scattered intensity, expressed as the average photopulse rate produced by the PMT detector, in the range of 100–500 kHz.

Hence, the automatic dilution system is designed to monitor quasi-continuously the scattered light intensity signal J, typically by means of monitoring the photopulse rate output of a high-sensitivity PMT detector 168, or other suitable detection device, which is responsive to the light signal J. The system then adjusts the particle concentration in the fluid stream exiting the SM device and entering scattering cell 156, in order to raise or lower the average scattered light intensity obtained from cell 156, by increasing or decreasing, respectively, the flow rate $F_{D3}$ of diluent fluid introduced into predilution chamber MC1, which causes prediluted sample suspension to exit chamber MC1 at the same flow rate and become mixed with diluent fluid flowing at rate $F_{D1}$ into the SM device, yielding a second dilution factor DF2 equal to $1+F_{D1}/F_{D3}$ in the usual way, as described earlier. Typically, the system is designed to recognize that a final, appropriate value of DF2 has been reached, following a suitable delay time of approximately $3\tau$ (where $\tau=V_{SM}/(F_{D1}+F_{D3})$, where $V_{SM}$ is the effective mixing volume of the SM device) following a change in the prediluted sample injection flow rate $F_{D3}$, as described above, when the average scattered light intensity reaches a value which lies within an acceptable, given percentage of a fixed, predetermined value—e.g. 300±100 kHz in the PMT photopulse rate.

When this intensity "endpoint" is reached, CPU/Controller 54, which is responsive to the PMT detector output photopulse signal (preconditioned additionally by means of a suitable amplifier and d.c. level discriminator electronic circuit 169) simultaneously instructs valve V14 to close and valve V6 to open, by means of control signals H9 and G9, respectively. This action allows a portion of the doubly-diluted sample suspension having a particle concentration appropriate for the ensuing DLS measurement to be captured in scattering cell 156 and the flow of diluted sample suspension to be diverted to SPOS sensor 16, allowing it to flow continuously through sensor 16 and pass through tubing 90 to a drain.

At this point in time, the automatic dilution system begins to readjust once again the value of the second dilution factor DF2 by means of adjusting the flow rate of injection $F_{D3}$ of diluent fluid into predilution chamber MC1, by means of delivery means 96, as instructed by control signal A9, as described in detail previously, so that an optimal (or otherwise desired) value is achieved for the particle concentration in the diluted sample suspension passing through SPOS sensor 16. Particle count and size data are collected and stored in the memory of CPU/Controller 54, and the resulting PSD for the SPOS subsystem is constructed and stored in memory for either immediate or subsequent display and other uses. After a suitable length of time has elapsed (either preset by the operator at the outset of the automatic dilution and measurement process, or determined from an analysis of the "quality" of the DLS results), the PSD obtained from the DLS subsystem is stored in memory for either immediate or subsequent display and other uses, separate from, or in conjunction with, the PSD obtained from the SPOS subsystem.

It should be understood that scattering intensity J obtained from the diluted sample suspension in scattering cell 156 changes with time following the start of the mixed-flow dilution process with the same functional dependence described by Equation 3, appropriate for the SPOS method. The difference now is that the t-dependent particle concentration C(t) is replaced by the t-dependent scattering intensity, denoted by J(t). The final value for the scattering intensity after equilibrium in static mixer SM in FIG. 10 (or stirred mixing chamber, if appropriate) has been reached (i.e. $t \gg \tau$) is denoted by $J_F$, which takes the place of the quantity ($C_0$/DF) in Equation 3 in the case of the SPOS method. Hence, for the DLS subsystem shown in FIG. 10, Equation 3 is effectively replaced by, $$J(t)=J_F[1-e^{(-t/\tau)}] \tag{9}$$

In analogy with the discussion earlier involving the SPOS method, one can determine the instantaneous rate of increase, also called R(t), of the scattering intensity and, from it, thereby make a relatively fast estimate of the final, equilibrium value $J_F$. In this case, R(t) is defined as the time derivative of J(t). From Equation 9 one calculates, $$R(t)=dJ(t)/dt=J_F(1/\tau)e^{(-t/\tau)} \tag{10}$$

The maximum rate, denoted by $R_{max}(0)$ as before, again occurs at t+0—i.e., immediately after the start of injection of prediluted sample suspension into static mixer SM in FIG. 10. This maximum rate is now given by, $$R_{max}(0)=J_F/\tau=J_F(F/V) \tag{11}$$

The final equilibrium value $J_F$ of the scattering intensity can then be obtained from $R_{max}(0)$, analogous to the procedure used to obtain the final diluted sample concentration $C_0$/DF in Equation 8 for SPOS, $$J_F=\tau R_{max}(0)=(V/F)R_{max}(0) \tag{12}$$

CPU/Controller 54 will have been programmed to increase or decrease dilution factor DF, as described earlier, by the numerical factor required to decrease or increase, respectively, the final estimated scattering intensity $J_F$ so that it falls within a preset range of values appropriate or optimal, for PMT means 168 or other suitable detector means, as described above.

It is to be observed that for sufficiently dilute sample suspensions the scattering intensity J is proportional to particle concentration and may be thus characterized as a quantity related to particle concentration.

It should be understood that this same description concerning estimation of $J_F$ from $R_{max}(0)$ also applies to the measurement method to be described below, which is an alternative to the DLS technique.

It should be understood that there is an alternative "ensemble" method, different from DLS but also based on light scattering, for characterizing the overall PSD of the sample, which can be employed in conjunction with the automatic dilution system of this invention, as described in connection with FIG. 10. The light scattering scheme shown in FIG. 10 utilizes a scattering angle of ninety degrees. However, this scheme can be generalized, and the angle varied, so that it can accommodate the method of classical, or "static", light scattering, as an alternative to dynamic light scattering (DLS).

In the classical, or Mie, scatting technique, the scattering intensity produced by a suitable dilute suspension of particles is measured as a function of scattering angle, over a suitable range of angles. The resulting intensity (averaged over time, to remove the effects of fluctuations due to difffusion) will, in general, vary with scattering angle due to intraparticle (Mie) interference of light waves. A suitable "inversion" algorithm is required to convert the angular dependent scattering intensity data to an approximate particle size distribution (PSD).

The light scattering subsystem shown in FIG. 10 can be easily modified so that it can be used to determine the PSD using classical light scattering. All that is required is to provide a means for systematically changing the scattering angle. For example, optimal element means 164 and optical fiber means 166 can together be mounted on a rigid arm which, in turn, is attached to the shaft of a stepper motor, whose axis of rotation coincides with the central (vertical) axis of scattering cell 156. The optical detection elements can then be located at any desired angle of scattering by applying an appropriate control signal, generated by CPU/Controller 54, to the stepper motor.

The system in FIG. 10, modified in this way, can be made to automatically "scan" optical elements 164 and 166 over a preselected intensity to be measured over an entire set of desired angles by PMT means 168. The signal for each angle is suitably conditioned (including smoothing over time) by means 169, processed by means 170 and stored either in CPU/Controller 54 or in an external computer. Processing means 170 can be used to calculate an approximate PSD for the sample by "inverting" the data of scattering intensity vs angle by means of an appropriate algorithm.

It should be pointed out that in this utilization of the scheme (suitably modified) of FIG. 10 to determine the PSD using classical light scattering, the automatic dilution system described earlier would establish an optimal value for factor DF by adjusting the final particle concentration so that the average scattering intensity at a particular angle, typically 90 degrees, would be adjusted to a particular value, intermediate in magnitude, allowing for substantial increase or decrease with changing angle. Unlike the case of DLS described above, the diluted sample suspension in scattering cell 156 can be either stationary or flowing for the method of classical light scattering.

It is to be understood that CPU/Controller 54 is suitably programmed to provide all of the functions which it performs as described above. These include the provision of an input menu for determining from the user the particular SPOS or other sensor used and for the particular application with which the apparatus is to be used the appropriate acceptable minimum statistical accuracy, determining from this data the optimal dilution factor, making all necessary computations, storing all necessary data, and generating all appropriate control signals, suitably timed, for controlling all of the functions of the apparatus as described. It is to be further understood that these functions may be provided, in whole or in part, by a suitably programmed external computer or computers.

Although the invention has been described with reference to particular embodiments and also with reference to modifications, alterative arrangements and variants of these embodiments, it is to be understood that the invention is not to be limited to these specific embodiments and modifications, but is only to be limited by the following claims.

I claim:

1. An automatic dilution system for providing an optimal value of dilution factor DF for a sample suspension containing particles mixed with a diluent, comprising:

means for providing a continuous flow of said diluent into mixing means;

means for injecting a continuous flow of said sample together with said diluent in said mixing means to provide a net combined flow of diluent and sample from said mixing means, said flow of said diluent being substantially larger than said flow of said sample, whereby said flow of said sample has a relatively minor effect on said net combined flow of said diluent and said sample and said net combined flow is substantially the value of said flow of diluent;

sensor means for measuring a value of a particular characteristic related to particle concentration of said diluted sample leaving said mixing means, said sensor means having a particle coincidence concentration limit;

controller means for determining from said value of said particular characteristic an optimal value of dilution factor DF needed to provide an optimal particle concentration in said diluted sample, said optimal particle concentration being the maximum particle concentration which does not exceed a desired percentage of said coincidence concentration limit of said sensor means, said controller means generating a control signal from said determined optimal value of dilution factor DF; and means responsive to said control signal for adjusting at least one of said flow of said sample and said flow of said diluent to provide said optimal value of dilution factor DF for said diluted sample in said mixing means.

2. An automatic dilution system for providing an optimal value of dilution factor DF for a sample suspension containing particles mixed with a diluent, comprising:

means for providing a continuous flow of said diluent into mixing means;

means for injecting a continuous flow of said sample together with said diluent in said mixing means;

sensor means for measuring a value of a particular characteristic related to particle concentration of said diluted sample leaving said mixing means, said sensor means having a particle coincidence concentration limit;

controller means for determining from said value of said particular characteristic an optimal value of dilution factor DF needed to provide an optimal particle concentration in said diluted sample, said optimal particle concentration being the maximum particle concentration which does not exceed a desired percentage of said coincidence concentration limit of said sensor means, said controller means generating a control signal from said determined optimal value of dilution factor DF; and means responsive to said control signal for adjusting at least one of said flow of said sample and said flow of said diluent to provide said optimal value of dilution factor DF for said diluted sample in said mixing means, wherein said particular characteristic of said diluted sample comprises the initial rate of increase $R_{max}(0)$ of a quantity related to particle concentration in said diluted sample in said mixing means.

3. The automatic dilution system of claim 2, wherein said particle concentration in said diluted sample is the particle concentration of a given range of particle sizes.

4. The automatic dilution system of claim 3, wherein said given range of sizes includes all particle sizes.

5. The automatic dilution system of claim 2, wherein said controller means calculates from the value of $R_{max}(0)$ the approximate final concentration of particles $C_0/DF$ expected when equilibrium is achieved in said mixing means, where $C_0$ is the initial concentration before dilution of given range of particle sizes, compares the computed value of $C_0/DF$ with said optimal particle concentration, determines from the comparison said optimal value of DF needed to achieve said optimal particle concentration, and generate said control signal.

6. The automatic dilution system of claim 1, wherein said mixing means comprises a mixing chamber including stirrer means.

7. The automatic dilution system of claim 1, wherein said sensor means is based on the principle of single-particle optical sensing.

8. The automatic dilution system of claim 7, wherein said means for injecting a flow of said sample into said mixing means comprises a sample delivery pump, and wherein said means for providing a flow of said diluent comprises a diluent delivery pump.

9. The automatic dilution system of claim 8, wherein said sample delivery pump is a variable output syringe pump.

10. The automatic dilution system of claim 1, wherein said adjusted flow of at least one of said sample and said diluent continues for a time sufficient to achieve equilibrium in the particle concentration in said diluted sample leaving said mixing means, and wherein said sensor means generates data for the construction of a particle size distribution of the sample.

11. The automatic dilution system of claim 1, wherein said mixing means comprises a mixing chamber, and wherein flow means causes a portion of the diluted sample in said mixing chamber to be directed to said sensing means, the remaining portion of said diluted sample being discarded.

12. The automatic dilution system of claim 11, wherein said flow means comprises a diluted sample pump.

13. The automatic dilution system of claim 12, wherein said diluted sample pump comprises a metering pump.

14. The automatic dilution system of claim 12, wherein said diluted sample pump is positioned between said mixing chamber and said sensing means.

15. The automatic dilution system of claim 12, wherein said sensing means is positioned between said mixing chamber and said diluted sample pump.

16. The automatic dilution system of claim 11, wherein said means for injecting a flow of said sample comprises a metering pump.

17. The automatic dilution system of claim 1, wherein said diluent flows in a diluent flow tube, wherein said mixing means comprises a static mixer of relatively small effective volume in series with said flow tube, wherein said means for injecting a flow of said sample comprises means for injecting said sample into said flow tube upstream from said static mixer, and wherein said sensor means is located downstream from said static mixer and receives said diluted sample from said static mixer.

18. The automatic dilution system of claim 17, wherein said means for injecting a flow of said sample further comprises a sample metering pump.

19. The automatic dilution system of claim 1, wherein said mixing means comprises a first mixing means for prediluting said sample and a second mixing means, flow means feeding the prediluted sample in said first mixing means to said second mixing means, wherein said means for injecting a flow of said sample feeds said sample into said first mixing means, and wherein said means for providing a flow of diluent includes first means to feed diluent to said first mixing means and second means for feeding diluent to said second mixing means.

20. The automatic dilution system of claim 19, wherein said flow means for feeding said prediluted sample to said second mixing means feeds diluent to said first mixing chamber means after it is filled with said sample and diluent supplied by said first means to push said prediluted sample into said second mixing means.

21. The automatic dilution system of claim 20, further comprising sample injection valve means and a length of tubing, and wherein said means for injecting a flow of sample fills said length of tubing with said sample, wherein said first means delivers diluent through said sample injection valve means and a diluent fluid path into said first mixing chamber means, and said means for injecting a flow of sample places said length of tubing in series with said diluent fluid path permitting injection of said sample in said loop of tubing into said first mixing chamber means as diluent fluid flows through said path.

22. The automatic dilution system of claim 21, wherein said flow means for feeding said prediluted sample comprises a syringe pump.

23. The automatic dilution system of claim 21, wherein said second mixing means feeds diluted sample to said sensor means.

24. The automatic dilution system of claim 23, further comprising an assisted-drain pump for draining diluted sample from said sensor means.

25. The automatic dilution system of claim 19, wherein diluent flow to said second mixing means flows in a diluent flow tube, wherein said second mixing means comprises a static mixer of relatively small volume in series with said diluent flow tube, and wherein said means for injecting a flow of sample comprises means for injecting said sample into said flow tube upstream from said static mixer, and wherein said sensor means is located downstream from said static mixer and receives said diluted sample from said static mixer.

26. The automatic dilution system of claim 1, wherein said diluted sample leaving said mixing me ans is fed to one of a pair of branches, first sensor means for measuring the value of a first said particular characteristic of said diluted sample in one of said branches and second sensor means for measuring a second said particular characteristic of said diluted sample in the other of said branches.

27. The automatic dilution system of claim 26, wherein said second sensor means senses light scattering and said second said particular characteristic is the initial rate of increase of light intensity in said diluted sample.

28. The automatic dilution system of claim 27, wherein said first sensor means is a single particle optical sensor and said first characteristic is the initial rate of increase of particle concentration in said diluted sample.

29. The automatic dilution system of claim 1, wherein said mixing means has a relatively short equilibrium time, and wherein said means responsive to said control signal responds so quickly that it operates virtually in a negative feedback mode.

30. The automatic dilution system of claim 29, wherein said mixing means is a static mixer having a relatively small volume.

31. The automatic dilution system of claim 29, wherein said mixing means comprises a first predilution chamber feeding a prediluted sample to a second dilution stage comprising a static mixer of relatively small volume, providing said short equilibrium time.

32. A method for automatically diluting a sample suspension containing particles with an optimal value of dilution factor DF, comprising:
   providing a continuous flow of diluent into mixing means;
   injecting a continuous flow of said sample into said mixing means;
   mixing said diluent and said sample in said mixing means to provide a diluted sample;
   measuring a value of a particular characteristic related to particle concentration of said diluted sample;
   determining from said value of said particular characteristic an optimal value of dilution factor DF to provide an optimal particle concentration in said diluted sample;
   generating a control signal from said determined optimal value of dilution factor DF; and
   in response to said control signal adjusting said flow of said sample to provide said optimal value of dilution factor DF in said mixing means.

33. The method of claim 32, wherein said particular characteristic of said diluted sample comprises the initial rate of increase $R_{max}(0)$ of a quantity related to particle concentration in said diluted sample in said mixing means.

34. The method of claim 33, wherein said particle concentration in, said diluted sample is the particle concentration of a given range of particle sizes.

35. The method of claim 34, wherein said given range of sizes include all particle sizes.

36. The method of claim 33, wherein said step of determining an optimal value of dilution factor DF from said value of said particular characteristic comprises calculating from the value of $R_{max}(0)$ the approximate final concentration of particles $C_0/DF$ expected when equilibrium is achieved in said mixing means, where $C_0$ is the initial concentration before dilution, comparing the computed value of $C_0/DF$ with said optimal particle concentration, determining from the comparison said optimal value of DF needed to achieve said optimal particle concentration, developing a control signal for adjusting said flow of sample to provide a new flow rate of sample to provide said optimal value of DF.

37. The method of claim 32, wherein said mixing means comprises a mixing chamber.

38. The method of claim 32, wherein said measuring step is based on the principal of single-particle optical sensing.

39. The method of claim 32, wherein said adjusted flow of sample and said flow of diluent is permitted to continue until equilibrium is achieved in the particle concentration and wherein said measuring step generates data for the construction of a particle size distribution of the sample.

40. The method of claim 32, further comprising the steps of withdrawing a portion of the dilute sample wherein said measuring step is applied to said portion.

41. The method of claim 32, wherein said mixing means comprises a static mixer connected in series with a flow tube, wherein said diluent is directed through said flow tube, wherein said sample is injected directly into said flow tube, upstream from said static mixer, and wherein said sample and said diluent are mixed in said static mixer.

42. The method of claim 32, wherein said mixing means comprises a first mixing means and a second mixing means, and wherein said method comprises prediluting said sample with said diluent in said first mixing means, feeding said prediluted sample to said second mixing means, and further diluting said prediluted sample in said second mixing means.

43. The method of claim 42, wherein said sample is placed in a length of tubing in series with said diluent, and wherein said sample and diluent are injected into said first mxng chamber, through a common flow tube.

44. The method of claim 42, further comprising the step of feeding additional diluent to said first mixing means after it is filled with prediluted sample to force said prediluted sample from said first mixing chamber to said second mixing chamber.

45. The method of claim 32, wherein said sample is prediluted and then further diluted.

46. An automatic diluting system for controlling the value of dilution factor DF for a concentrated sample suspension containing particles mixed with a diluent, comprising:
   means for providing a flow of diluent into mixing means;
   means for injecting a flow of a concentrated sample suspension into said mixing means to dilute said sample;
   sensor means for determining the particle count rate of said diluted sample leaving said mixing means;
   means for deriving a control signal from said count rate; and
   means responsive to said control signal for adjusting one of said flow of concentrated sample suspension and said flow of diluent to adjust said dilution factor DF, said flows of diluent and sample suspension into said mixing means being continuous.

47. The automatic dilution system of claim 46, wherein said means for deriving a control signal comprises means for determining the initial rate of increase of particle concentration after mixing of said sample in said diluent begins.

48. The automatic dilution system of claim 47, wherein said means for deriving a control signal further comprises computing from said initial rate of increase of particles the approximate final concentration of particles expected when equilibrium is achieved in said mixing means, comparing said computed approximate final concentration of particles with an optimum particle concentration for said sensor means and, determining from said comparison the optimum value of dilution factor needed to achieve said optimal particle concentration.

49. An automatic dilution system for controlling the dilution factor DF for a concentrated sample suspension containing particles mixed with a diluent, comprising,
   means providing a continuous flow of diluent into mixing means;
   sample delivery means for delivering a flow of said concentrated sample suspension at a continuous flow rate $F_S$ into said mixing means to dilute said sample;
   sensor means for determining the particle concentration per unit volume of said diluted sample leaving said mixing means; and
   means for deriving a control signal from said particle concentration per unit volume;

said sample delivery means being responsive to said control signal for adjusting said flow rate $F_S$ of said concentrated sample suspension to adjust said dilution factor DF.

50. A method for automatically diluting a sample suspension, comprising:

feeding a diluent fluid into mixing means;

initially injecting a sample suspension to be diluted into a capture loop; and then feeding a diluent fluid at a controlled, adjustable flow rate into one end of said capture loop to force said sample suspension undiluted from said the other end of said capture loop into said mixing means.

51. A method for automatically diluting a sample suspension, comprising:

prediluting said sample suspension in first mixing means with a diluent fluid to provide a prediluted sample suspension;

continuously adding diluent fluid at a controlled, adjustable rate to said mixing means to force said prediluted sample out of said first mixing means into second mixing means; and further diluting said prediluted sample in said second mixing means by continuously feeding a diluent at a controlled, adjustable flow rate into said second mixing means.

52. A method for automatically diluting a sample suspension having a particle size distribution characteristic with tail portions at its upper and lower ends, comprising:

setting the starting threshold diameter to limit examination of said sample suspension to a range of particle sizes in one of said tail portions;

measuring the particle concentration in said range of particle sizes in said one of said tail portions; and adjusting the dilution factor of said sample in response to said measurement.

53. The method of claim 32, wherein said mixing means has a relatively short equilibrium time, and wherein said adjustment of said flow of said sample responds so quickly that it operates virtually in a negative feedback mode.

* * * * *